(12) United States Patent
Harvey et al.

(10) Patent No.: US 7,908,091 B2
(45) Date of Patent: Mar. 15, 2011

(54) METHODS OF PREDICTING AND MONITORING TYROSINE KINASE INHIBITOR THERAPY

(75) Inventors: Jeanne Harvey, Livermore, CA (US); Bruce Neri, Carlsbad, CA (US); Sharat Singh, Los Altos Hills, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 713 days.

(21) Appl. No.: 11/687,254

(22) Filed: Mar. 16, 2007

(65) Prior Publication Data

US 2007/0254295 A1    Nov. 1, 2007

Related U.S. Application Data

(60) Provisional application No. 60/829,812, filed on Oct. 17, 2006, provisional application No. 60/783,743, filed on Mar. 17, 2006.

(51) Int. Cl.
*G06F 7/00* (2006.01)
(52) U.S. Cl. ............... 702/19; 702/20; 703/11; 703/12; 703/13; 707/700; 435/6; 436/501
(58) Field of Classification Search .................. None
See application file for complete search history.

(56) References Cited

U.S. PATENT DOCUMENTS

2005/0164196 A1*  7/2005  Dressman et al. ............. 435/6
2006/0115827 A1*  6/2006  Lenz ............................. 435/6

FOREIGN PATENT DOCUMENTS

WO     WO03/087404      * 10/2003
WO     WO 2006/108627 A1   10/2006

OTHER PUBLICATIONS

Demetri et al., J. Clin. Oncol. ASCO Annual Meeting Proc., 23:4000 (2005)).*
Kakiuchi et al.; Prediction of sensitivity of advanced non-small cell lung cancers to gefitinib (Iressa, ZD1839); Human Molecular Genetics; 2004; vol. 13, No. 24; pp. 3029-3043.*
Moasser, The Tyrosine Kinase Inhibitor ZD1839 ("Iressa") Inhibits HER2-driven Signaling and Suppresses the Growth of HER2-overexpressing Tumor Cells; Oct. 1, 2001; Cancer Research 61; pp. 7184-7188.
Okano, et al.; Proteomic Signature Corresponding to the Response to Gefitinib, and Epidermal Growth Factor Receptor Tyrosine Kinase Inhibitor in Lung Adenocarcinoma; 2007; Clin Cancer Res.13(3): 799-805.
Cappuzzo, et al.; Epidermal Growth Factor Receptor Gene and Protein and Gefitinib Sensitivity in Non-Small-Cell Lung Cancer; Journal of the National Cancer Institute; 2005; vol. 97, No. 9: 643-655.
Heinrich; Molecular basis for treatment of gastrointestinal stromal tumours; EJC Supplements; 2006; vol. 4, suppl. 1: 10-18.

* cited by examiner

*Primary Examiner* — Mary K Zeman
(74) *Attorney, Agent, or Firm* — Kilpatrick, Townsend & Stockton LLP

(57) ABSTRACT

The present invention provides methods for analyzing a combination of biomarkers to individualize tyrosine kinase inhibitor therapy in patients who have been diagnosed with cancer. In particular, the assay methods of the present invention are useful for predicting, identifying, or monitoring the response of a tumor, tumor cell, or patient to treatment with a tyrosine kinase inhibitor using an algorithm based upon biomarker profiling. The assay methods of the present invention are also useful for predicting whether a patient has a risk of developing toxicity or resistance to treatment with a tyrosine kinase inhibitor. In addition, the assay methods of the present invention are useful for monitoring tyrosine kinase inhibitor therapy in a patient receiving the drug to evaluate whether the patient will develop resistance to the drug. Furthermore, the assay methods of the present invention are useful for optimizing the dose of a tyrosine kinase inhibitor in a patient receiving the drug to achieve therapeutic efficacy and/or reduce toxic side-effects.

19 Claims, 3 Drawing Sheets

METHODS OF PREDICTING AND MONITORING TYROSINE KINASE INHIBITOR THERAPY

CROSS-REFERENCES TO RELATED APPLICATIONS

This application claims priority to U.S. Provisional Application No. 60/783,743, filed Mar. 17, 2006, and U.S. Provisional Application No. 60/829,812, filed Oct. 17, 2006, the disclosures of which are hereby incorporated by reference in their entirety for all purposes.

BACKGROUND OF THE INVENTION

Tyrosine kinases are a class of enzymes that catalyze the transfer of the terminal phosphate of adenosine triphosphate (ATP) to tyrosine residues in protein substrates. Tyrosine kinases are believed, by way of substrate phosphorylation, to play critical roles in signal transduction for a number of cell functions. In fact, tyrosine kinases have been shown to be important contributing factors in cell proliferation, carcinogenesis, and cell differentiation. Tyrosine kinases can be categorized as either receptor tyrosine kinases or non-receptor tyrosine kinases.

Receptor tyrosine kinases are key regulators of intercellular communication that controls cell growth, proliferation, differentiation, survival, and metabolism. About 20 different receptor tyrosine kinase families have been identified that share a similar structure, namely an extracellular binding site for ligands, a transmembrane region, and an intracellular tyrosine kinase domain (see, e.g., Ullrich et al., Cell, 61:203-212 (1990); Pawson, Eur. J. Cancer, 38(Supp 5):S3-S10 (2002)). For example, the EGFR family of receptor tyrosine kinases comprises EGFR/HER1/ErbB1, HER2/Neu/ErbB2, HER3/ErbB3, and HER4/ErbB4. Ligands of this family of receptors include epithelial growth factor (EGF), TGF-$\alpha$ amphiregulin, HB-EGF, betacellulin, and heregulin. Other receptor tyrosine kinase families include the PDGF family, the FLK family, and the insulin family of receptors.

Extracellular ligand binding of receptor tyrosine kinases induces or stabilizes receptor dimerization, leading to increased kinase activity. The intracellular catalytic domain displays the highest level of conservation among receptor tyrosine kinases, includes the ATP-binding site that catalyzes receptor autophosphorylation of cytoplasmic tyrosine residues, and serves as the docking site for Src homology 2 (SH2)- and phosphotyrosine-binding (PTB) domain-containing proteins such as Grb2, Shc, Src, Cb 1, and phospholipase C-$\gamma$. These proteins subsequently recruit additional effectors containing SH2-, SH3-, PTB-, and pleckstrin-homology (PH) domains to the activated receptor, which results in the assembly of signaling complexes at the membrane and the activation of a cascade of intracellular biochemical signals. The most important downstream signaling cascades activated by receptor tyrosine kinases include the Ras/Raf/mitogen activated protein (MAP) kinase pathway, the phosphoinositide 3-kinase/Akt pathway, and the JAK/STAT pathway. The complex signaling network triggered by receptor tyrosine kinases eventually leads either to activation or repression of various subsets of genes and thus defines the biological response to a given signal.

The activity of receptor tyrosine kinases and their signaling cascades is precisely coordinated and tightly controlled in normal cells. However, deregulation of the receptor tyrosine kinase signaling system, either by stimulation through growth factor and/or through genetic alteration, produces deregulated tyrosine kinase activity. These aberrations generally result in receptor tyrosine kinases with constitutive or strongly enhanced kinase activity and subsequent signaling capacity, which leads to malignant transformation. Therefore, they are frequently linked to human cancer and also to other hyperproliferative diseases such as psoriasis (Robertson et al., Trends Genet., 16:265-271 (2000)). The most important mechanisms leading to constitutive receptor tyrosine kinase signaling include overexpression and/or gene amplification, genetic alterations such as deletions and mutations within the extracellular domain or catalytic site, and autocrine-paracrine stimulation through aberrant growth factor loops.

More particularly, gene amplification and/or overexpression of receptor tyrosine kinases occurs in many human cancers, which might increase the response of cancer cells to normal growth factor levels. Additionally, overexpression of a specific receptor tyrosine kinase on the cell surface increases the incidence of receptor dimerization, even in the absence of an activating ligand. In many cases, this results in constitutive activation of the receptor tyrosine kinase, leading to aberrant and uncontrolled cell proliferation and tumor formation. For example, EGFR/HER1/ErbB1 is frequently overexpressed in non-small cell lung, bladder, cervical, ovarian, kidney, and pancreatic cancer as well as in squamous cell carcinomas of the head and neck (Hong et al., Oncol. Biother., 1:1-29 (2000)). The predominant mechanism leading to EGFR overexpression is gene amplification, with up to about 60 copies per cell reported in certain tumors (Libermann et al., Nature, 313:144-147 (1985)). In general, elevated levels of EGFR expression are associated with high metastatic rate and increased tumor proliferation (Pavelic et al., Anticancer Res., 13:1133-1138 (1993)). Therefore, receptor tyrosine kinases such as EGFR are recognized as attractive targets for the design and development of compounds that can specifically inhibit their tyrosine kinase activity in cancer cells.

Small molecule tyrosine kinase inhibitors compete with the ATP-binding site of the catalytic domain of target tyrosine kinases. Such inhibitors are generally orally active and have a favorable safety profile that can easily be combined with other forms of cancer therapy. Several tyrosine kinase inhibitors have been identified to possess effective antitumor activity and have been approved or are in clinical trials. These include gefitinib (Iressa®), sunitinib (Sutent®; SU11248), erlotinib (Tarceva®; OSI-1774), lapatinib (GW-572016), canertinib (CI 1033), semaxinib (SU5416), vatalanib (PTK787/ZK222584), sorafenib (BAY 43-9006), imatinib mesylate (Gleevec®; STI571), and leflunomide (SU101). Although tyrosine kinase inhibitors represent a new class of targeted therapy that interferes with specific cell signaling pathways and allows target-specific therapy for selected malignancies, there is currently a lack of tumor response to these inhibitors in the general population. For example, only about 10% of patients with non-small cell lung cancer in whom standard therapy failed respond to the EGFR inhibitor gefitinib (Fukuoka et al., J. Clin. Oncol., 21:2237-2246 (2003); Kris et al., JAMA, 290:2149-2158 (2003)). In addition, patients may be at risk of toxicity to tyrosine kinase inhibitors. Furthermore, tyrosine kinase inhibitor therapy is typically very expensive in comparison to conventional chemotherapy. Moreover, resistance to tyrosine kinase inhibitors can manifest during treatment, and sometimes a particular inhibitor becomes wholly ineffective in certain patients.

As a result, due to the high cost of tyrosine kinase inhibitor therapy, the small percentage of responders, the risk of toxic side-effects, and the possibility of developing resistance during treatment, it is imperative to prescribe tyrosine kinase inhibitors only to those patients for whom such therapy will have some benefit. Thus, there is a need in the art for methods that utilize a combination of biomarkers to predict a patient's response to tyrosine kinase inhibitors such as EGFR inhibitors. There is also a need in the art for methods that utilize a combination of biomarkers to identify patients who are at greater risk of developing toxicity to tyrosine kinase inhibitors and to reduce the toxic effects of tyrosine kinase inhibitors in patients already receiving the drug. There is a further need in the art for methods that utilize a combination of biomarkers to identify patients with acquired resistance to tyrosine kinase inhibitor therapy in recurring tumors. The present invention satisfies these needs and provides related advantages as well.

BRIEF SUMMARY OF THE INVENTION

The present invention provides methods for analyzing a combination of biomarkers to individualize tyrosine kinase inhibitor therapy in patients who have been diagnosed with cancer. In particular, the assay methods of the present invention are useful for predicting, identifying, or monitoring the response of a tumor, tumor cell, or patient to treatment with a tyrosine kinase inhibitor using an algorithm based upon biomarker profiling. The assay methods of the present invention are also useful for predicting whether a patient has a risk of developing toxicity or resistance to treatment with a tyrosine kinase inhibitor. In addition, the assay methods of the present invention are useful for monitoring tyrosine kinase inhibitor therapy in a patient receiving the drug to evaluate whether the patient will develop resistance to the drug. Furthermore, the assay methods of the present invention are useful for optimizing the dose of a tyrosine kinase inhibitor in a patient receiving the drug to achieve therapeutic efficacy and/or reduce toxic side-effects.

In one aspect, the present invention provides an assay method for identifying the response of a tumor to treatment with a tyrosine kinase inhibitor, the method comprising:
(a) determining at least one profile selected from the group consisting of a nucleic acid profile, protein profile, and combinations thereof in a sample from a subject; and
(b) identifying the tumor as responsive or non-responsive to treatment with the tyrosine kinase inhibitor using an algorithm based upon the at least one profile.

In another aspect, the present invention provides an assay method for predicting the response of a subject to treatment with a tyrosine kinase inhibitor, the method comprising:
(a) determining at least one profile selected from the group consisting of a nucleic acid profile, protein profile, and combinations thereof in a sample from the subject; and
(b) predicting the likelihood that the subject will respond to treatment with the tyrosine kinase inhibitor using an algorithm based upon the at least one profile.

In yet another aspect, the present invention provides an assay method for monitoring treatment with a tyrosine kinase inhibitor in a subject, the method comprising:
(a) determining at least one profile selected from the group consisting of a nucleic acid profile, protein profile, and combinations thereof in a sample from the subject; and
(b) monitoring the likelihood that the subject will develop resistance to treatment with the tyrosine kinase inhibitor using an algorithm based upon the at least one profile.

In a further aspect, the present invention provides an assay method for optimizing dose efficacy in a subject receiving a tyrosine kinase inhibitor, the method comprising:
(a) determining at least one profile selected from the group consisting of a nucleic acid profile, protein profile, and combinations thereof in a sample from the subject; and
(b) recommending a subsequent dose of the tyrosine kinase inhibitor using an algorithm based upon the at least one profile.

Other objects, features, and advantages of the present invention will be apparent to one of skill in the art from the following detailed description and figures.

DETAILED DESCRIPTION OF THE INVENTION

I. Introduction

Figure 1:
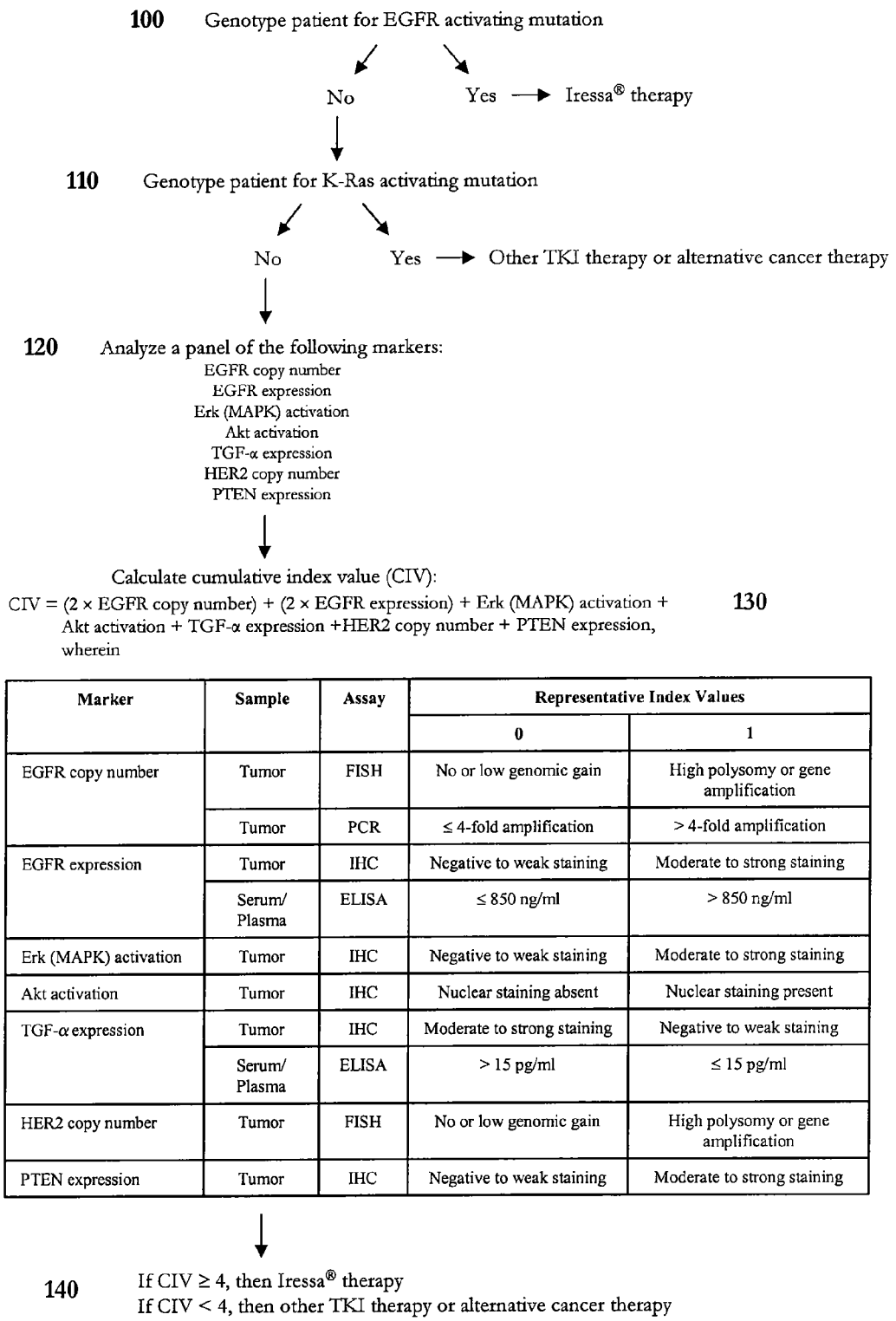
FIG. 1 shows a flowchart of one embodiment of the present invention describing an algorithm for individualizing gefitinib (Iressa®) therapy in patients with cancer.

The present invention is based, in part, on the surprising discovery that a combination of biomarkers can be used in an algorithmic approach to individualize tyrosine kinase inhibitor therapy in patients with cancers comprising solid tumors such as colorectal cancer, lung cancer, etc. Given the high inter-patient variability in response to tyrosine kinase inhibitors, the assay methods of the present invention are particularly advantageous because they utilize a combinatorial strategy that takes into account differences in nucleic acid and/or protein profiles of multiple molecular determinants (i.e., biomarkers) to determine whether a tumor or tumor cell from a patient has a high likelihood of responding to treatment with a specific tyrosine kinase inhibitor or combination of tyrosine kinase inhibitors. If the patient is classified as a responder, a dosing regimen tailored to that patient can then be created to achieve therapeutic efficacy without inducing toxic side-effects. Consequently, patients classified as responders can receive the full benefits of tyrosine kinase inhibitor therapy without experiencing the side-effects associated with such therapy. Similarly, patients already undergoing treatment with a tyrosine kinase inhibitor can experience a reduction in toxic side-effects without compromising therapeutic efficacy by adjusting the subsequent dose of the drug. Likewise, patients already undergoing treatment with a tyrosine kinase inhibitor can be monitored to assess whether resistance to the drug has developed and an alternative cancer therapy should be administered. As a result, the methods of the present invention enable tyrosine kinase inhibitors such as gefitinib and sunitinib to become first-line therapeutic agents, rather than their current role as second- or third-line cancer therapies. The tyrosine kinase inhibitors described herein can be administered alone or co-administered (e.g., concurrently or sequentially) with conventional chemotherapy, radiation therapy, hormonal therapy, and/or immunotherapy for the treatment of cancer.

Currently, tumor tissue is analyzed using various individual biomarkers to give an indication of the appropriate therapy in patients with solid tumors. For example, HER2 or EGFR immunohistochemistry on tumor tissue is performed prior to prescribing trastuzumab (Herceptin®) or cetuximab (Erbitux®), respectively. However, there are substantial limitations associated with the use of tumor tissue for biomarker analysis. In particular, tumor tissue is only available pre-surgery or in patients without surgical therapy, formalin-fixation paraffin-embedding of tumor tissue interferes with the analysis of many biomarkers, variability in fixation processing alters the level of many biomarkers in tumor tissue, and for small tumors, as are increasingly detected in breast cancer, very little tumor tissue sample is left for biomarker analysis after standard pathology. In addition, tumor tissue is not available during the course of tyrosine kinase inhibitor therapy, so it cannot be used for monitoring efficacy or determining when a change in therapy is needed. The present invention overcomes these limitations by utilizing fractional components obtained from a single sample. As a non-limiting example, a whole blood sample which is separated into its liquid (e.g., plasma, serum, etc.) and cellular (e.g., red blood cells, white blood cells, platelets, etc.) components can be analyzed for an entire spectrum of biomarkers, thereby providing an advantageous means of individualizing tyrosine kinase inhibitor therapy according to the methods of the present invention.

As such, the present invention provides more accurate methods for predicting, identifying, or monitoring the response of a tumor (e.g., lung carcinoma, colorectal carcinoma, gastrointestinal stromal tumor, renal cell carcinoma, etc.), a tumor cell (e.g., a circulating tumor cell or circulating endothelial cell derived from a tumor), or a patient who has been diagnosed with cancer to treatment with a specific tyrosine kinase inhibitor (e.g., gefitinib, sutent, etc.) or cocktail of tyrosine kinase inhibitors. The present invention is also useful for monitoring the development of acquired resistance to treatment with one or more tyrosine kinase inhibitors in a patient who has been receiving the drug. In addition, the present invention finds utility in methods of optimizing tyrosine kinase inhibitor dosages (e.g., optimizing dose amount, optimizing dose efficacy, reducing drug toxicity, etc.) in patients undergoing tyrosine kinase inhibitor therapy.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; breast cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells.

The term "tyrosine kinase" as used herein includes enzymes that catalyze the transfer of the terminal phosphate of adenosine triphosphate (ATP) to tyrosine residues in protein substrates. Non-limiting examples of tyrosine kinases include receptor tyrosine kinases such as EGFR (e.g., EGFR/HER1/ErbB1, HER2/Neu/ErbB2, HER3/ErbB3, HER4/ErbB4), INSR (insulin receptor), IGF-IR, IGF-II1R, IRR (insulin receptor-related receptor), PDGFR (e.g., PDGFRA, PDGFRB), c-KIT/SCFR, VEGFR-1/FLT-1, VEGFR-2/FLK-1/KDR, VEGFR-3/FLT-4, FLT-3/FLK-2, CSF-1R, FGFR 1-4, CCK4, TRK A-C, MET, RON, EPHA 1-8, EPHB 1-6, AXL, MER, TYRO3, TIE, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106; and non-receptor tyrosine kinases such as BCR-ABL, Src, Frk, Btk, Csk, Abl, Zap70, Fes/Fps, Fak, Jak, Ack, and LIMK. One of skill in the art will know of other receptor and/or non-receptor tyrosine kinases that can be targeted using the inhibitors described herein.

The term "tyrosine kinase inhibitor" includes any of a variety of therapeutic agents or drugs that act as selective or non-selective inhibitors of receptor and/or non-receptor tyrosine kinases. Without being bound to any particular theory, tyrosine kinase inhibitors generally inhibit target tyrosine kinases by binding to the ATP-binding site of the enzyme. Examples of tyrosine kinase inhibitors suitable for use in the methods of the present invention include, but are not limited to, gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), derivatives thereof, analogs thereof, and combinations thereof. Additional tyrosine kinase inhibitors suitable for use in the present invention are described in, e.g., U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340. One of skill in the art will know of other tyrosine kinase inhibitors suitable for use in the present invention. In certain instances, the tyrosine kinase inhibitor is administered in a pharmaceutically acceptable form including, without limitation, an alkali or alkaline earth metal salt such as an aluminum, calcium, lithium, magnesium, potassium, sodium, or zinc salt; an ammonium salt such as a tertiary amine or quaternary ammonium salt; and an acid salt such as a succinate, tartarate, bitartarate, dihydrochloride, salicylate, hemisuccinate, citrate, isocitrate, malate, maleate, mesylate, hydrochloride, hydrobromide, phosphate, acetate, carbamate, sulfate, nitrate, formate, lactate, gluconate, glucuronate, pyruvate, oxalacetate, fumarate, propionate, aspartate, glutamate, or benzoate salt.

As used herein, the term "biomarker" or "marker" includes any biochemical marker, serological marker, genetic marker, or other clinical or echographic characteristic that can be used in predicting, identifying, evaluating, assessing, determining, monitoring, and/or optimizing tyrosine kinase inhibitor efficacy, toxicity, and/or resistance according to the methods of the present invention. Examples of biochemical or serological markers include, without limitation, tyrosine kinases such as the receptor and non-receptor tyrosine kinases described above; growth factors (e.g., TGF-α, EGF, VEGF, PDGF, amphiregulin, HB-EGF (heparin-binding EGF-like growth factor), betacellulin, heregulin, etc.); tumor suppressors (e.g., PTEN (phosphatase and tensin homolog deleted on chromosome 10), DMBT1 (deleted in malignant brain tumors 1), LGI1 (leucine-rich gene-glioma inactivated 1), p53, etc.); and tyrosine kinase signaling components (e.g., Akt, MAPK/ERK, MEK, RAF, PLA2, MEKK, JNKK, JNK, p38, PI3K, Ras, Rho, PLC, PKC, p70 S6 kinase, p53, cyclin D1, STAT1, STAT3, PIP2, PIP3, PDK, mTOR, BAD, p21, p27, ROCK, IP3, TSP-1, NOS, etc.). Examples of genetic markers include, without limitation, tyrosine kinases such as the receptor and non-receptor tyrosine kinases described above and small GTPases such as Ras (e.g., K-Ras, N-Ras, H-Ras, etc.), Rho, Rac1, and Cdc42. In some embodiments, the genetic markers described herein are genotyped to detect the presence or absence of a variant allele, e.g., an activating mutation. Preferably, one or more biochemical or serological markers are measured in combination with one or more genetic markers. One skilled in the art will appreciate that biochemical or serological markers can also be categorized as genetic markers and vice versa.

As used herein, the term "profile" includes any set of data that represents the distinctive features or characteristics associated with a tumor, tumor cell, and/or cancer. The term encompasses a "nucleic acid profile" that analyzes one or more genetic markers, a "protein profile" that analyzes one or more biochemical or serological markers, and combinations thereof. Examples of nucleic acid profiles include, but are not limited to, a genotypic profile, gene copy number profile, gene expression profile, DNA methylation profile, and combinations thereof. Non-limiting examples of protein profiles include a protein expression profile, protein activation profile, and combinations thereof. For example, a "genotypic profile" includes a set of genotypic data that represents the genotype of one or more genes associated with a tumor, tumor cell, and/or cancer. Similarly, a "gene copy number profile" includes a set of gene copy number data that represents the amplification of one or more genes associated with a tumor, tumor cell, and/or cancer. Likewise, a "gene expression profile" includes a set of gene expression data that represents the mRNA levels of one or more genes associated with a tumor, tumor cell, and/or cancer. In addition, a "DNA methylation profile" includes a set of methylation data that represents the DNA methylation levels (e.g., methylation status) of one or more genes associated with a tumor, tumor cell, and/or cancer. Furthermore, a "protein expression profile" includes a set of protein expression data that represents the levels of one or more proteins associated with a tumor, tumor cell, and/or cancer. Moreover, a "protein activation profile" includes a set of data that represents the activation (e.g., phosphorylation status) of one or more proteins associated with a tumor, tumor cell, and/or cancer.

The term "gene" includes the segment of DNA involved in producing a polypeptide chain. Specifically, a gene includes, without limitation, regions preceding and following the coding region, such as the promoter and 3'-untranslated region, respectively, as well as intervening sequences (introns) between individual coding segments (exons).

The term "nucleic acid" or "polynucleotide" includes deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, and mRNA encoded by a gene.

The term "polymorphism" include the occurrence of two or more genetically determined alternative sequences or alleles in a population. A "polymorphic site" includes the locus at which divergence occurs. Preferred polymorphic sites have at least two alleles, each occurring at frequency of greater than 1%, and more preferably greater than 10% or 20% of a selected population. A polymorphic locus can be as small as one base pair (single nucleotide polymorphism, or SNP) or can comprise an insertion or deletion of multiple nucleotides. Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele and other alleles are designated as alternative or "variant alleles." The allele occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "genotype" as used herein includes to the genetic composition of an organism, including, for example, whether a diploid organism is heterozygous or homozygous for one or more variant alleles of interest.

The term "gene amplification" comprises a cellular process characterized by the production of multiple copies of any particular piece of DNA. For example, a tumor cell amplifies, or copies, chromosomal segments naturally as a result of cell signals and sometimes environmental events. The process of gene amplification leads to the production of many copies of the genes that are located on that region of the chromosome. In certain instances, so many copies of the amplified region are produced that they can form their own small pseudochromosomes called double-minute chromosomes. The genes on each of the copies can be transcribed and translated, leading to an overproduction of the mRNA and protein corresponding to the amplified genes.

The term "subject" or "patient" typically includes humans, but can also include other animals such as, e.g., other primates, rodents, canines, felines, equines, ovines, porcines, and the like.

The term "sample" as used herein includes any biological specimen obtained from a subject. Samples include, without limitation, whole blood, plasma, serum, red blood cells, white blood cells (e.g., peripheral blood mononuclear cells), saliva, urine, stool (i.e., feces), tears, nipple aspirate, lymph, fine needle aspirate, any other bodily fluid, a tissue sample (e.g., tumor tissue) such as a biopsy of a tumor, and cellular extracts thereof. In some embodiments, the sample is whole blood or a fractional component thereof such as plasma, serum, or a cell pellet. In preferred embodiments, the sample is obtained by isolating circulating cells of a solid tumor from a whole blood cell pellet using any technique known in the art. As used herein, the term "circulating cells" comprises cells that have either metastasized or micrometastasized from a solid tumor and includes circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.). In other embodiments, the sample is a formalin fixed paraffin embedded (FFPE) tumor tissue sample, e.g., from a solid tumor of the lung, colon, or rectum.

The term "course of therapy" or "therapy" includes any therapeutic approach taken to relieve and/or prevent one or more symptoms associated with cancer. The term encompasses administering any compound, drug, therapeutic agent, procedure, or regimen useful for improving the health of a subject with cancer. One skilled in the art will appreciate that either the course of therapy or the dose of the current course of therapy can be changed based upon the panel of biomarkers determined using the methods of the present invention. Examples of therapies suitable for use in the methods of the present invention include, without limitation, targeted cancer therapy using tyrosine kinase inhibitors, conventional chemotherapy, radiation therapy, hormonal therapy, immunotherapy, and combinations thereof.

The term "recommending" as used herein includes providing dosing instructions for a tyrosine kinase inhibitor or alternative cancer therapy based on the nucleic acid and/or protein profiles determined for a particular subject. In some embodiments, the methods of the present invention provide a recommendation of an initial dose of the drug. In other embodiments, the methods of the present invention provide a recommendation of a subsequent dose of the drug or an alternative therapy. Dosing instructions include, without limitation, lab results with preferred drug doses, data sheets, lookup tables setting forth preferred drug doses, instructions or guidelines for using the drug, package inserts to accompany the drug, and the like. In certain embodiments, the term "recommending" associates the result obtained from the use of a particular algorithm (e.g., index value) with side-effects or efficacy.

As used herein, the term "administering" includes oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a tyrosine kinase inhibitor is administered at the same time, just prior to, or just after the administration of one or more additional drugs or therapeutic regimens (e.g., other tyrosine kinase inhibitors; other anticancer agents such as chemotherapeutic agents, monoclonal antibodies, antibiotics, immunosuppressive agents, and anti-inflammatory agents; other cancer therapies such as radiation therapy, hormonal therapy, and immunotherapy; etc.).

The term "identifying the response of a tumor to treatment with a tyrosine kinase inhibitor" includes the use of the algorithms of the present invention to determine whether a tumor or tumor cell is responsive (i.e., sensitive) or non-responsive (i.e., resistant) to the effects of a particular tyrosine kinase inhibitor or combinations thereof. Generally, a tumor or tumor cell which is responsive to treatment with a tyrosine kinase inhibitor exhibits an improvement in one or more desired results (e.g., tumor cell death, inhibition of tumor growth, reduction in tumor size, prevention of tumor metastasis, etc.) when compared to the absence of treatment in control samples. In certain instances, a tumor or tumor cell is considered to be responsive to treatment with a tyrosine kinase inhibitor when it responds to initial treatment but then develops resistance as treatment is continued.

The term "predicting the response of a subject to treatment with a tyrosine kinase inhibitor" includes the use of the algorithms of the present invention to determine whether a subject would likely respond to a particular tyrosine kinase inhibitor or combinations thereof. Although cancer is used herein as a non-limiting example, one skilled in the art will appreciate that subjects having other diseases or disorders in which tyrosine kinase inhibitors provide some therapeutic benefit can also be evaluated according to the methods of the present invention. Generally, a patient who is responsive to treatment with a tyrosine kinase inhibitor exhibits an improvement in one or more desired clinical results (e.g., alleviation of symptoms, diminishment of the extent of cancer, stabilization of cancer, delaying or slowing the progression of cancer, amelioration of cancer, remission, etc.) when compared to the absence of treatment (e.g., placebo) in control patients. In certain instances, a patient is considered to be responsive to treatment with a tyrosine kinase inhibitor when that patient responds to initial treatment but then develops resistance as treatment is continued.

The term "monitoring treatment with a tyrosine kinase inhibitor in a subject" includes the use of the algorithms of the present invention to determine whether a subject will develop or has developed resistance to treatment with a tyrosine kinase inhibitor. In certain instances, the result obtained from the use of a particular algorithm indicates that the subject has an increased likelihood of developing or has developed resistance to tyrosine kinase inhibitor therapy. In certain other instances, the result obtained from the use of a particular algorithm indicates that the subject has a decreased likelihood of developing or has not developed resistance to tyrosine kinase inhibitor therapy.

The term "optimizing dose efficacy in a subject receiving a tyrosine kinase inhibitor" includes the use of the algorithms of the present invention to adjust the subsequent dose of the tyrosine kinase inhibitor or to change the course of therapy for a subject after the drug has been administered in order to optimize its therapeutic efficacy. In certain instances, the result obtained from the use of a particular algorithm indicates that the subsequent dose of the tyrosine kinase inhibitor should be increased, decreased, or maintained. In certain other instances, the result obtained from the use of a particular algorithm indicates that an alternative cancer therapy should be administered to the subject.

III. Description of the Embodiments

The present invention provides methods for analyzing a combination of biomarkers in a sample such as whole blood to individualize tyrosine kinase inhibitor therapy in subjects who have been diagnosed with cancer. As a result, the present invention enables tyrosine kinase inhibitors such as gefitinib and sunitinib to become first-line therapeutic agents for the treatment of solid tumors, rather than their current role as second- or third-line cancer therapies.

Accordingly, in one aspect, the present invention provides an assay method for identifying the response of a tumor to treatment with a tyrosine kinase inhibitor, the method comprising:

(a) determining at least one profile selected from the group consisting of a nucleic acid profile, protein profile, and combinations thereof in a sample from a subject; and (b) identifying the tumor as responsive or non-responsive to treatment with the tyrosine kinase inhibitor using an algorithm based upon the at least one profile.

In one embodiment, the tumor comprises a solid tumor of a tissue selected from the group consisting of lung, colon, rectum, gall bladder, brain, breast, kidney, pancreas, stomach, liver, bone, skin, spleen, ovary, testis, prostate, and muscle. Preferably, the tumor is non-small cell lung carcinoma, a gastrointestinal stromal tumor, colorectal carcinoma, or renal cell carcinoma. In another embodiment, the subject has been diagnosed with cancer.

In some embodiments, the sample comprises a whole blood, serum, plasma, urine, nipple aspirate, lymph, saliva, fine needle aspirate, and/or tumor tissue sample. In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs) and circulating endothelial cells (CECs). The plasma or serum fraction usually contains, inter alia, nucleic acids (e.g., DNA, RNA) and proteins that are released by CTCs and/or CECs. The circulating cells can be isolated using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), microfluidic separation (see, e.g., Mohamed et al., *IEEE Trans. Nanobiosci.*, 3:251-256 (2004)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)). In some instances, the isolated circulating cells can be stimulated in vitro with one or more growth factors before, during, and/or after incubation with one or more tyrosine kinase inhibitors of interest. In other instances, the isolated circulating cells can be lysed, e.g., following growth factor stimulation, to produce a cellular extract (e.g., tumor cell lysate) using any technique known in the art.

In other embodiments, the tyrosine kinase inhibitor comprises an epidermal growth factor receptor (EGFR) inhibitor, vascular endothelial cell growth factor receptor (VEGFR) inhibitor, platelet-derived growth factor receptor (PDGFR) inhibitor, c-KIT inhibitor, FMS-like tyrosine kinase 3 (FLT-3) inhibitor, BCR-ABL inhibitor, and combinations thereof. Examples of EGFR inhibitors include, but are not limited to, gefitinib, erlotinib, lapatinib, canertinib, sorafenib, vandetanib, pharmaceutically acceptable salts thereof, and combinations thereof. Non-limiting examples of VEGFR inhibitors include sunitinib, semaxinib, vatalanib, sorafenib, vandetanib, pharmaceutically acceptable salts thereof, and combinations thereof. Examples of PDGFR inhibitors include, without limitation, sunitinib, imatinib, sorafenib, leflunomide, pharmaceutically acceptable salts thereof, and combinations thereof. Non-limiting examples of c-KIT inhibitors include sunitinib, imatinib, semaxinib, pharmaceutically acceptable salts thereof, and combinations thereof. Examples of FLT-3 inhibitors include, but are not limited to, sunitinib, semaxinib, pharmaceutically acceptable salts thereof, and combinations thereof. Examples of BCR-ABL inhibitors include, without limitation, imatinib and a pharmaceutically acceptable salt thereof.

In another embodiment, the nucleic acid profile comprises a genotypic profile, gene copy number profile, gene expression profile, DNA methylation profile, and combinations thereof.

In certain instances, the genotypic profile comprises determining the genotype of at least one gene selected from the group consisting of a tyrosine kinase gene, small GTPase gene, and combinations thereof. The genotype can be determined at a polymorphic site such as a single nucleotide polymorphism (SNP). In a preferred embodiment, the tyrosine kinase gene is selected from the group consisting of an EGFR gene, VEGFR gene, PDGFR gene, c-KIT gene, FLT-3 gene, BCR-ABL gene, and combinations thereof. Examples of EGFR genes include, but are not limited to, an EGFR (HER1/ErbB1) gene, HER2 (Neu/ErbB2) gene, HER3 (ErbB3) gene, HER4 (ErbB4) gene, and combinations thereof. Non-limiting examples of small GTPase genes include a Ras gene, Rho gene, Rac1 gene, Cdc42 gene, and combinations thereof. Preferably, the Ras gene is selected from the group consisting of a K-Ras gene, N-Ras gene, H-Ras gene, and combinations thereof.

In certain instances, the gene copy number profile comprises determining the number of copies of at least one tyrosine kinase gene. In a preferred embodiment, the at least one tyrosine kinase gene is selected from the group consisting of an EGFR gene, VEGFR gene, PDGFR gene, c-KIT gene, FLT-3 gene, BCR-ABL gene, and combinations thereof. As a non-limiting example, gene amplification can be detected in one or more members of the EGFR family of genes, e.g., EGFR (HER1/ErbB1), HER2 (Neu/ErbB2), HER3 (ErbB3), and/or HER4 (ErbB4). Preferably, the number of copies of said at least one tyrosine kinase gene is determined by fluorescence in situ hybridization (FISH). Alternatively, gene amplification can be measured using chromogenic in situ hybridization (CISH) or immunohistochemistry (IHC).

In certain instances, the gene expression profile comprises determining the expression level of at least one tyrosine kinase gene. The expression level of any of the tyrosine kinase genes described herein can be analyzed. Preferably, the expression level of the at least one tyrosine kinase gene is determined by measuring mRNA levels.

In certain instances, the DNA methylation profile comprises determining the methylation state of at least one tumor suppressor gene. As a non-limiting example, DNA methylation can be detected in tumor suppressor genes such as PTEN, DMBT1, LGI1, p53, CDKN2B, ESR1 (human estrogen receptor 1), ICSBP (interferon consensus-binding protein), ETV3 (Ets variant 3), DDX20 (DEAD box polypeptide), and combinations thereof. The level of DNA methylation can be measured using any method known to one of skill in the art, such as those techniques described below.

In a further embodiment, the protein profile comprises a protein expression profile, protein activation profile, and combinations thereof.

In certain instances, the protein expression profile comprises determining the expression level of at least one protein selected from the group consisting of a tyrosine kinase, growth factor, tumor suppressor, and combinations thereof. In a preferred embodiment, the tyrosine kinase is selected from the group consisting of EGFR, VEGFR, PDGFR, c-KIT, FLT-3, BCR-ABL, and combinations thereof. As a non-limiting example, an expression level can be measured for one or more members of the EGFR family, e.g., EGFR (HER1/ErbB1), HER2 (Neu/ErbB2), HER3 (ErbB3), and/or HER4

(ErbB4). Examples of growth factors include, but are not limited to, TGF-α, EGF, VEGF, PDGF, and combinations thereof. Non-limiting examples of tumor suppressors include PTEN, DMBT1, LGI1, and combinations thereof. Preferably, the expression level of the at least one protein is determined by IHC or an immunoassay such as an enzyme-linked immunosorbent assay (ELISA).

In certain instances, the protein activation profile comprises determining the phosphorylation state, ubiquitination state, and/or complexation state of at least one protein selected from the group consisting of a tyrosine kinase, tyrosine kinase signaling component, and combinations thereof. In one embodiment, the tyrosine kinase is selected from the group consisting of EGFR, VEGFR, PDGFR, c-KIT, FLT-3, BCR-ABL, and combinations thereof. As a non-limiting example, the complexation state of members of the EGFR family, e.g., EGFR (HER1/ErbB1), HER2 (Neu/ErbB2), HER3 (ErbB3), and/or HER4 (ErbB4), can be determined by detecting the presence or level of one or more EGFR heterodimeric complexes (e.g., ErbB2:EGFR, ErbB2:ErbB3, ErbB2:ErbB4, etc.). In another embodiment, the at least one tyrosine kinase signaling component is selected from the group consisting of Akt, MAPK/ERK, MEK, RAF, PLA2, MEKK, JNKK, JNK, p38, PI3K, Ras, Rho, PLC, PKC, p70 S6 kinase, p53, cyclin D1, STAT1, STAT3, PIP2, PIP3, PDK, mTOR, BAD, p21, p27, ROCK, IP3, TSP-1, NOS, and combinations thereof. In some instances, the phosphorylation state of the tyrosine kinase and/or tyrosine kinase signaling component can be determined by IHC. Other techniques include performing an immunoassay such as an ELISA to assess the phosphorylation state of one or more proteins of interest.

In another embodiment, the algorithm is used to calculate an index value. In certain instances, the index value comprises a cumulative index value. Typically, the cumulative index value is compared to an index cutoff value. In certain instances, a cumulative index value that is greater than or equal to the index cutoff value indicates that the subject is responsive or has an increased likelihood of responding to treatment with the tyrosine kinase inhibitor. In these instances, the method can further comprise recommending a dose (e.g., a therapeutically effective dose) of the tyrosine kinase inhibitor to be administered to the subject. In certain other instances, a cumulative index value that is greater than or equal to the index cutoff value indicates that the subject is non-responsive or has a decreased likelihood of responding to treatment with the tyrosine kinase inhibitor. In these instances, the method can further comprise recommending a dose of another tyrosine kinase inhibitor or an alternative cancer therapy to be administered to the subject.

In some embodiments, identifying a tumor as responsive or non-responsive to treatment with a tyrosine kinase inhibitor is based upon determining at least one nucleic acid and/or protein profile in conjunction with the use of a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a neural network (e.g., artificial NN (ANN), etc.).

In certain instances, the algorithm comprises a single learning statistical classifier system. Preferably, the single learning statistical classifier system comprises a tree-based statistical algorithm such as a RF or C&RT or a neural network such as an ANN. As a non-limiting example, a single learning statistical classifier system can be used to identify the tumor as responsive or non-responsive to treatment based upon a prediction or probability value and the at least one nucleic acid and/or protein profile. The use of a single learning statistical classifier system typically identifies the tumor as sensitive or resistant to the tyrosine kinase inhibitor of interest with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain other instances, the algorithm comprises a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the at least one nucleic acid and/or protein profile, and a NN can then be used to identify the tumor as responsive or non-responsive to treatment with a tyrosine kinase inhibitor based upon the prediction or probability value and the at least one nucleic acid and/or protein profile. Advantageously, the hybrid RF/NN learning statistical classifier system of the present invention identifies the tumor as sensitive or resistant to the tyrosine kinase inhibitor of interest with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain embodiments, the methods of the present invention further comprise sending the identification results (i.e., whether the tumor is responsive or non-responsive to treatment with the tyrosine kinase inhibitor) to a clinician, e.g., an oncologist or a general practitioner.

In another aspect, the present invention provides an assay method for predicting the response of a subject to treatment with a tyrosine kinase inhibitor, the method comprising:
  (a) determining at least one profile selected from the group consisting of a nucleic acid profile, protein profile, and combinations thereof in a sample from the subject; and
  (b) predicting the likelihood that the subject will respond to treatment with the tyrosine kinase inhibitor using an algorithm based upon the at least one profile.

In one embodiment, the subject has been diagnosed with cancer, e.g., a solid tumor of a tissue selected from the group consisting of lung, colon, rectum, gall bladder, brain, breast, kidney, pancreas, stomach, liver, bone, skin, spleen, ovary, testis, prostate, and muscle. Preferably, the cancer is non-small cell lung cancer, a gastrointestinal stromal tumor, colorectal cancer, or renal cell carcinoma.

In some embodiments, the sample comprises a whole blood, serum, plasma, urine, nipple aspirate, lymph, saliva, fine needle aspirate, and/or tumor tissue sample. In certain instances, the whole blood sample is separated into a plasma or serum fraction and a cellular fraction (i.e., cell pellet). The circulating cells of the solid tumor can be isolated from the cellular fraction using one or more of the separation methods described above. In some instances, the isolated circulating cells can be stimulated in vitro with one or more growth factors before, during, and/or after incubation with one or more tyrosine kinase inhibitors of interest. In other instances, the isolated circulating cells can be lysed, e.g., following growth factor stimulation, to produce a cellular extract (e.g., tumor cell lysate) using any technique known in the art.

In other embodiments, the tyrosine kinase inhibitor is selected from the group consisting of an EGFR inhibitor, VEGFR inhibitor, PDGFR inhibitor, c-KIT inhibitor, FLT-3 inhibitor, BCR-ABL inhibitor, and combinations thereof. Examples of inhibitors belonging to each class are described above.

In another embodiment, the nucleic acid profile is selected from the group consisting of a genotypic profile, gene copy number profile, gene expression profile, DNA methylation profile, and combinations thereof. In a further embodiment, the protein profile is selected from the group consisting of a protein expression profile, protein activation profile, and combinations thereof. Non-limiting examples of techniques that can be used to determine these nucleic acid and protein profiles are described above.

In some embodiments, the algorithm is used to calculate an index value. In certain instances, the index value comprises a cumulative index value. Typically, the cumulative index value is compared to an index cutoff value. In certain instances, a cumulative index value that is greater than or equal to the index cutoff value indicates that the subject has an increased likelihood of responding to treatment with the tyrosine kinase inhibitor. In these instances, the method can further comprise recommending a dose (e.g., a therapeutically effective dose) of the tyrosine kinase inhibitor to be administered to the subject. In certain other instances, a cumulative index value that is greater than or equal to the index cutoff value indicates that the subject has a decreased likelihood of responding to treatment with the tyrosine kinase inhibitor. In these instances, the method can further comprise recommending a dose of another tyrosine kinase inhibitor or an alternative cancer therapy to be administered to the subject.

In some embodiments, predicting the likelihood that a subject will respond to treatment with a tyrosine kinase inhibitor is based upon determining at least one nucleic acid and/or protein profile in conjunction with the use of a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a neural network (e.g., artificial NN (ANN), etc.).

In certain instances, the algorithm comprises a single learning statistical classifier system. As a non-limiting example, a single learning statistical classifier system can be used to predict the likelihood that the subject will respond to treatment based upon a prediction or probability value and the at least one nucleic acid and/or protein profile. The use of a single learning statistical classifier system typically predicts the likelihood that the subject will respond to the tyrosine kinase inhibitor of interest with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain other instances, the algorithm comprises a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the at least one nucleic acid and/or protein profile, and a NN can then be used to predict the likelihood that the subject will respond to treatment with a tyrosine kinase inhibitor based upon the prediction or probability value and the at least one nucleic acid and/or protein profile. Advantageously, the hybrid RF/NN learning statistical classifier system of the present invention predicts the likelihood that the subject will respond to the tyrosine kinase inhibitor of interest with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain embodiments, the methods of the present invention further comprise sending the prediction results (i.e., whether the subject is likely to respond to treatment with the tyrosine kinase inhibitor) to a clinician, e.g., an oncologist or a general practitioner.

In yet another aspect, the present invention provides an assay method for monitoring treatment with a tyrosine kinase inhibitor in a subject, the method comprising:
(a) determining at least one profile selected from the group consisting of a nucleic acid profile, protein profile, and combinations thereof in a sample from the subject; and
(b) monitoring the likelihood that the subject will develop resistance to treatment with the tyrosine kinase inhibitor using an algorithm based upon the at least one profile.

In one embodiment, the subject has been diagnosed with cancer, e.g., a solid tumor of a tissue selected from the group consisting of lung, colon, rectum, gall bladder, brain, breast, kidney, pancreas, stomach, liver, bone, skin, spleen, ovary, testis, prostate, and muscle. Preferably, the cancer is non-small cell lung cancer, a gastrointestinal stromal tumor, colorectal cancer, or renal cell carcinoma.

In some embodiments, the sample comprises a whole blood, serum, plasma, urine, nipple aspirate, lymph, saliva, fine needle aspirate, and/or tumor tissue sample. In certain instances, the whole blood sample is separated into a plasma or serum fraction and a cellular fraction (i.e., cell pellet). The circulating cells of the solid tumor can be isolated from the cellular fraction using one or more of the separation methods described above. In some instances, the isolated circulating cells can be stimulated in vitro with one or more growth factors before, during, and/or after incubation with one or more tyrosine kinase inhibitors of interest. In other instances, the isolated circulating cells can be lysed, e.g., following growth factor stimulation, to produce a cellular extract (e.g., tumor cell lysate) using any technique known in the art.

In other embodiments, the tyrosine kinase inhibitor is selected from the group consisting of an EGFR inhibitor, VEGFR inhibitor, PDGFR inhibitor, c-KIT inhibitor, FLT-3 inhibitor, BCR-ABL inhibitor, and combinations thereof. Examples of inhibitors belonging to each class are described above.

In another embodiment, the nucleic acid profile is selected from the group consisting of a genotypic profile, gene copy number profile, gene expression profile, DNA methylation profile, and combinations thereof. In a further embodiment, the protein profile is selected from the group consisting of a protein expression profile, protein activation profile, and combinations thereof. Non-limiting examples of techniques that can be used to determine these nucleic acid and protein profiles are described above.

In some embodiments, the algorithm is used to calculate an index value. In certain instances, the index value comprises a cumulative index value. Typically, the cumulative index value is compared to an index cutoff value. In certain instances, a cumulative index value that is greater than or equal to the index cutoff value indicates that the subject has an increased likelihood of developing or has developed resistance to treatment with the tyrosine kinase inhibitor. In these instances, the method can further comprise recommending a dose of another tyrosine kinase inhibitor or an alternative therapy to be administered to the subject. In certain other instances, a cumulative index value that is greater than or equal to the index cutoff value indicates that the subject has a decreased likelihood of developing or has not developed resistance to treatment with the tyrosine kinase inhibitor. In these instances, the method can further comprise recommending that a subsequent dose of the tyrosine kinase inhibitor be maintained.

In other embodiments, the method can further comprise comparing the cumulative index value to a cumulative index value generated at an earlier time. In certain instances, an increase in the cumulative index value indicates that the subject has an increased likelihood of developing or has developed resistance to treatment with the tyrosine kinase inhibitor. In certain other instances, an increase in the cumulative index value indicates that the subject has a decreased likelihood of developing or has not developed resistance to treatment with the tyrosine kinase inhibitor.

In some embodiments, monitoring the likelihood that a subject will develop resistance to treatment with a tyrosine kinase inhibitor is based upon determining at least one nucleic acid and/or protein profile in conjunction with the use of a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a neural network (e.g., artificial NN (ANN), etc.).

In certain instances, the algorithm comprises a single learning statistical classifier system. As a non-limiting example, a single learning statistical classifier system can be used to monitor the likelihood that the subject will develop resistance to treatment based upon a prediction or probability value and the at least one nucleic acid and/or protein profile. The use of a single learning statistical classifier system typically monitors the likelihood that the subject will develop resistance to the tyrosine kinase inhibitor of interest with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In certain other instances, the algorithm comprises a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the at least one nucleic acid and/or protein profile, and a NN can then be used to monitor the likelihood that the subject will develop resistance to treatment with a tyrosine kinase inhibitor based upon the prediction or probability value and the at least one nucleic acid and/or protein profile. Advantageously, the hybrid RF/NN learning statistical classifier system of the present invention monitors the likelihood that the subject will develop resistance to the tyrosine kinase inhibitor of interest with a sensitivity, specificity, positive predictive value, negative predictive value, and/or overall accuracy of at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain embodiments, the methods of the present invention further comprise sending the monitoring results (i.e., whether the subject is likely to develop resistance to treatment with the tyrosine kinase inhibitor) to a clinician, e.g., an oncologist or a general practitioner.

In a further aspect, the present invention provides an assay method for optimizing dose efficacy in a subject receiving a tyrosine kinase inhibitor, the method comprising:
  (a) determining at least one profile selected from the group consisting of a nucleic acid profile, protein profile, and combinations thereof in a sample from the subject; and
  (b) recommending a subsequent dose of the tyrosine kinase inhibitor using an algorithm based upon the at least one profile.

In one embodiment, the subject has been diagnosed with cancer, e.g., a solid tumor of a tissue selected from the group consisting of lung, colon, rectum, gall bladder, brain, breast, kidney, pancreas, stomach, liver, bone, skin, spleen, ovary, testis, prostate, and muscle. Preferably, the cancer is non-small cell lung cancer, a gastrointestinal stromal tumor, colorectal cancer, or renal cell carcinoma.

In some embodiments, the sample comprises a whole blood, serum, plasma, urine, nipple aspirate, lymph, saliva, fine needle aspirate, and/or tumor tissue sample. In certain instances, the whole blood sample is separated into a plasma or serum fraction and a cellular fraction (i.e., cell pellet). The circulating cells of the solid tumor can be isolated from the cellular fraction using one or more of the separation methods described above. In some instances, the isolated circulating cells can be stimulated in vitro with one or more growth factors before, during, and/or after incubation with one or more tyrosine kinase inhibitors of interest. In other instances, the isolated circulating cells can be lysed, e.g., following growth factor stimulation, to produce a cellular extract (e.g., tumor cell lysate) using any technique known in the art.

In other embodiments, the tyrosine kinase inhibitor is selected from the group consisting of an EGFR inhibitor, VEGFR inhibitor, PDGFR inhibitor, c-KIT inhibitor, FLT-3 inhibitor, BCR-ABL inhibitor, and combinations thereof. Examples of inhibitors belonging to each class are described above.

In another embodiment, the nucleic acid profile is selected from the group consisting of a genotypic profile, gene copy number profile, gene expression profile, DNA methylation profile, and combinations thereof. In a further embodiment, the protein profile is selected from the group consisting of a protein expression profile, protein activation profile, and combinations thereof. Non-limiting examples of techniques that can be used to determine these nucleic acid and protein profiles are described above.

In some embodiments, the algorithm is used to calculate an index value. In certain instances, the index value comprises a cumulative index value. Typically, the cumulative index value is compared to an index cutoff value. In certain instances, a cumulative index value that is greater than or equal to the index cutoff value indicates that the subsequent dose of the tyrosine kinase inhibitor should be increased. In certain other instances, a cumulative index value that is greater than or equal to the index cutoff value indicates that the subsequent dose of the tyrosine kinase inhibitor should be decreased or an alternative cancer therapy should be administered. The method can further comprise recommending the subsequent dose (i.e., higher, lower, or the same) of the tyrosine kinase inhibitor to be administered or a dose of the alternative cancer therapy to be administered to the subject.

In some embodiments, recommending a subsequent dose of a tyrosine kinase inhibitor is based upon determining at least one nucleic acid and/or protein profile in conjunction with the use of a learning statistical classifier system. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a neural network (e.g., artificial NN (ANN), etc.).

In certain instances, the algorithm comprises a single learning statistical classifier system. In certain other instances, the algorithm comprises a combination of at least two learning statistical classifier systems. Preferably, the combination of learning statistical classifier systems comprises a RF and a NN, e.g., used in tandem or parallel.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

In certain embodiments, the methods of the present invention further comprise sending the recommendation results to a clinician, e.g., an oncologist or a general practitioner.

IV. Tyrosine Kinase Inhibitors

Tyrosine kinase inhibitors represent a class of therapeutic agents or drugs that target receptor and/or non-receptor tyrosine kinases in cells such as tumor cells. In certain instances, the tyrosine kinase inhibitor is an antibody-based (e.g., anti-tyrosine kinase monoclonal antibody, etc.) or polynucleotide-based (e.g., tyrosine kinase antisense oligonucleotide, small interfering ribonucleic acid, etc.) form of targeted therapy. Preferably, the tyrosine kinase inhibitor is a small molecule that inhibits target tyrosine kinases by binding to the ATP-binding site of the enzyme. Examples of small molecule tyrosine kinase inhibitors include, but are not limited to, gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), pharmaceutically acceptable salts thereof, derivatives thereof, analogs thereof, and combinations thereof. Additional examples of tyrosine kinase inhibitors suitable for use in the present invention include quinazolines (e.g., PD 153035,4-(3-chloroanilino)quinazoline, etc.), pyridopyrimidines, pyrimidopyrimidines, pyrrolopyrimidines (e.g., CGP 59326, CGP 60261, CGP 62706, etc.), pyrazolopyrimidines, 4-(phenylamino)-7H-pyrrolo[2,3-d]pyrimidines, curcumin (diferuloyl methane), 4,5-bis(4-fluoroanilino)phthalimide, tyrphostines containing nitrothiophene moieties, quinoxalines (see, e.g., U.S. Pat. No. 5,804,396), tryphostins (see, e.g., U.S. Pat. No. 5,804,396), PD0183805, PKI-166, EKB-569, IMC-1C11, Affinitac™ (LY900003; ISIS 3521), and the tyrosine kinase inhibitors described in PCT Publication Nos. WO 99/09016, WO 98/43960, WO 97/38983, WO 99/06378, WO 99/06396, WO 96/30347, WO 96/33978, WO 96/33979, and WO 96/33980.

As described herein, tyrosine kinase inhibitor therapy is generally limited by low response rates, the development of acquired resistance, and/or toxic side-effects. As a result, tyrosine kinase inhibitors currently find use only as second- or third-line cancer therapies. However, the methods of the present invention for predicting or identifying response and/or toxicity to tyrosine kinase inhibitors and monitoring resistance to tyrosine kinase inhibitor therapy advantageously enable tyrosine kinase inhibitors to be used in the first-line treatment of cancer.

Gefitinib (Iressa®) is a selective EGFR (HER1/ErbB1) tyrosine kinase inhibitor, exhibiting a 200-fold greater affinity for EGFR than for HER2 (Neu/ErbB2) (Thomas et al., *Cancer Treat. Revs.*, 30:255-268 (2004)). It prevents autophosphorylation of EGFR in a variety of tumor cell lines and xenografts (Arteaga et al., *Curr. Opin. Oncol.*, 6:491-498 (2001)). Gefitinib can also inhibit the growth of some HER2-overexpressing tumor cells (e.g., breast cancer cells) (Moulder et al., *Cancer Res.*, 61:8887-8895 (2001); Normanno et al., *Ann. Oncol.*, 13:65-72 (2002)) and tumor neoangiogenesis (Arteaga et al., supra).

Gefitinib is currently approved for the treatment of patients with non-small cell lung cancer after failure of both platinum-based and docetaxel chemotherapies. However, most patients with non-small cell lung cancer have no response to gefitinib. In fact, the response rate was only about 10% in large scale Phase II trials of patients with refractory disease (Fukuoka et al., *J. Clin. Oncol.*, 21:2237-2246 (2003); Kris et al., *JAMA*, 290:2149-2158 (2003)). Side-effects observed after gefitinib administration are generally mild and resolve after discontinuation of the drug. The most common adverse effects associated with gefitinib therapy include diarrhea, rash, acne, dry skin, nausea, vomiting, pruritus, anorexia, and asthenia (Dancey et al., *Lancet*, 362:62-64 (2003)). Other toxic side-effects include fatigue, elevated serum transaminase levels, stomatitis, bone pain, dyspnea, and pulmonary toxicity such as interstitial lung disease (i.e., alveolitis), pneumonitis, and interstitial pneumonia (Cersosimo, *Am. J. Health-Syst. Pharm.*, 61:889-898 (2004)).

Erlotinib (Tarceva®; OSI-1774) is another selective EGFR (HER1/ErbB1) tyrosine kinase inhibitor (Ranson, *Br. J. Cancer*, 90:2250-2255 (2004); Moyer et al., *Cancer Res.*, 57:4838-4848 (1997)). It inhibits EGF-dependent cell proliferation at nanomolar concentrations and blocks cell cycle progression in the G1 phase (Moyer et al., supra). Erlotinib was approved by the FDA in November, 2004. In a placebo-controlled trial, patients randomized to erlotinib with advanced stage III or IV non-small cell lung cancer and who had progressive disease after standard chemotherapies showed a low response rate of only 12% and a median survival of 8.4 months (Perez-Soler, *Clin. Cancer Res.*, 10:4238s-4240s (2004)). The most common side-effects observed with erlotinib include an acneiform skin rash and diarrhea. In fact, diarrhea is a dose-limiting adverse event. Other side-effects include headache, mucositis, hyperbilirubinemia, neutropenia, and anemia (Ranson et al., *J. Clin. Oncol.*, 20:2240-2250 (2002); Ranson, *Br. J. Cancer*, 90:2250-2255 (2004)).

Lapatinib (GW572016; GW2016) is a tyrosine kinase inhibitor of both EGFR (HER1/ErbB1) and HER2 (Neu/ErbB2). It has been shown to have activity against EGFR-, HER2-, and Akt-overexpressing human tumor xenografts (Rusnak et al., *Mol. Cancer. Ther.*, 1:85-94 (2001)). In fact, its non-selective inhibition of several receptor tyrosine kinases may account for a broader spectrum of antitumor activity and improved efficacy, with a lower likelihood of developing resistance. The most common side-effects observed with lapatinib include diarrhea and skin rash.

Canertinib (CI 1033) is a non-selective tyrosine kinase inhibitor that produces irreversible inhibition of all members of the EGFR family (Ranson, Br. J. Cancer, 90:2250-2255 (2004)). It has been shown to have activity against a variety of human breast carcinomas in tumor xenograft models (Allen et al., *Semin. Oncol.*, 29:11-21 (2002)). However, one Phase II trial in patients with refractory ovarian cancer has revealed that canertinib only possesses minimal antitumor activity (Campos et al., *J. Clin. Oncol. ASCO Annual Meeting Proc.*, 22:5054 (2004)).

Sunitinib (Sutent®; SU11248) is a broad spectrum orally available multi-targeted tyrosine kinase inhibitor of VEGFR, PDGFR, c-KIT, and FLT-3 (Mendel et al., *Proc. Am. Soc. Clin. Oncol.*, 21:94 (2002)). It inhibits the growth of a variety of mouse tumor cells and xenograft models (Bergsland, *Am. J. Health-Syst. Pharm.*, 61:S4-S11 (2004); Traxler et al., *Cancer Res.*, 64:4931-4941 (2004)). Tumor regression and antiangiogenic activity have been observed in Phase I trials, and Phase II studies in patients with metastatic kidney cancer have revealed that 33% of patients had a partial response and 37% had stable disease for longer than 3 months on sunitinib therapy (Eskens, *Br. J. Cancer*, 90:1-7 (2004); Motzer et al., *J. Clin. Oncol. ASCO Annual Meeting Proc.*, 22:4500 (2004)). Sunitinib has also been shown to delay the time of tumor progression and significantly reduce the death rate of imatinib-resistant gastrointestinal stromal tumors (Demetri et al., *J. Clin. Oncol. ASCO Annual Meeting Proc.*, 23:4000 (2005)).

Semaxinib (SU5416) is a non-selective tyrosine kinase inhibitor of VEGFR-2, c-KIT, and FLT-3 (Mendel et al., *Clin. Cancer Res.*, 6:4848-4858 (2000)). In a multi-center Phase II trial with twice weekly administration of semaxinib, only 1 complete and 7 partial responses were observed in patients with refractory acute myeloid leukemia (Fiedler et al., *Blood*, 102:2763-2767 (2003)). In addition, minimal objective response rates were observed in Phase II studies of patients with prostate cancer, renal cell carcinoma, or multiple myeloma. Toxic side-effects of semaxinib therapy include headache, nausea, vomiting, asthenia, pain at the infusion site, phlebitis, change in voice, and fever.

Vatalanib (PTK787/ZK222584) is a selective inhibitor of VEGF-1 (FLT-1) and VEGFR-2 (FLK-1/KDR). At higher concentrations, it also inhibits other tyrosine kinases such as PDGFR-β, c-KIT, and C-FMS (Lin et al., *Cancer Res.*, 2:5019-5026 (2002)). Studies on vatalanib have focused on its use in treating colorectal cancer, liver cancer, advanced prostate cancer, advanced renal cell carcinoma, and relapsed/refractory glioblastoma (Steward et al, *Proc. Am. Soc. Clin. Oncol.*, 22:1098 (2003); George et al., *Clin. Cancer Res.*, 7:548 (2001); Bergsland, *Am. J. Health-Syst. Pharm.*, 61:S4-S11 (2004)). However, partial and minor responses to vatalanib were observed in only 5% and 15% of patients with renal cell carcinoma, respectively (Rini et al., *J. Clin. Oncol.*, 23:1028-1043 (2005)). Toxic side-effects of vatalanib therapy include ataxia, vertigo, hypertension, and venous thromboembolism (Eskens, *Br. J. Cancer*, 90:1-7 (2004)).

Sorafenib (BAY 43-9006) is a RAF kinase and VEGFR, EFGR, and PDGFR tyrosine kinase inhibitor that blocks tumor cell proliferation and angiogenesis (Wilhelm et al., *Cancer Res.*, 64:7099-7109 (2004); Strumberg et al., *J. Clin. Oncol.*, 23:965-972 (2005)). It has significant activity in renal, colon, pancreatic, lung, and ovarian tumors (Wilhelm et al., supra). A Phase II randomized clinical trial in patients with advanced kidney cancer showed a statistically higher percentage of patients whose disease did not progress after a 12-week treatment period with sorafenib compared to the placebo group (Ratain et al., *J. Clin. Oncol. ASCO Annual Meeting Proc.*, 22:4501 (2004)). The most common side-effects of sorafenib therapy include skin reactions such as hand-foot syndrome and rash, diarrhea, fatigue, weight loss, and hypertension.

Imatinib (Gleevecs; STI571) is an inhibitor of the ABL, BCR-ABL, c-KIT, and PDGFR tyrosine kinases (Druker et al., *Nat. Med.*, 5:561-566 (1996)). It is used for the treatment of Philadelphia chromosome-positive patients with chronic myeloid leukemia who are either newly diagnosed or have failed interferon-α therapy (Kantarjian et al., *N. Engl. J. Med.*, 346:645-652 (2002); Druker et al., *N. Engl. J. Med.*, 344:1038-1042 (2001)). For example, imatinib therapy induced major cytogenetic responses in patients with chronic myeloid leukemia and is also effective in the treatment of adult acute lymphoblastic leukemia (Kantarjian et al., *Clin. Cancer Res.*, 8:2177-2187 (2002); Druker et al., *N. Engl. J. Med.*, 344:1038-1042 (2001)). In some patients, however, white blood cells become resistant to imatinib, resulting in relapse. Several clinical trials have also shown a significant response to imatinib in patients with advanced gastrointestinal stromal tumors (Druker, *Adv. Cancer Res.*, 91:1-35 (2004)). In fact, imatinib is now approved for the treatment of patients with c-KIT-positive unresectable and/or malignant gastrointestinal stromal tumors. Toxic side-effects associated with imatinib therapy include neutropenia, thrombocytopenia, anemia, nausea, skin rash, peripheral edema, muscle cramps, and elevated liver transaminase levels (Kantarjian et al., *N. Engl. J. Med.*, 346:645-652 (2002)).

Leflunomide (SU101) is a small molecule inhibitor of PDGFR-mediated phosphorylation and thus inhibits PDGF-mediated cell signaling (Shawver et al., *Clin. Cancer Res.*, 3:1167-1177 (1997)). A Phase II study in patients with hormone refractory prostate cancer indicated that administration of leflunomide resulted in partial responses in less than 5% of patients and a decrease in prostate specific antigen of greater than 50% in only about 7% of patients (Ko et al., *Clin. Cancer Res.*, 4:800-805 (2001)). The most common side-effects include asthenia, nausea, anorexia, and anemia.

Although the dose of a tyrosine kinase inhibitor administered to a patient varies with the cancer being treated, the dose should generally be between about 1 mg/day to about 800 mg/day, and preferably, between about 100 mg/day to about 400 mg/day. For example, the recommended dose of orally administered gefitinib for patients with non-small cell lung cancer is between about 200 mg/day to about 300 mg/day, and preferably about 250 mg/day. As another example, the recommended dose of orally administered sunitinib for patients with gastrointestinal stromal tumors or renal cell carcinoma is between about 20 mg/day to about 100 mg/day, and preferably about 50 mg/day. Higher doses may be required in patients with more advanced tumors. Doses can be given at any time of the day, with or without food. Adjustments of dosage, if necessary, can be made according to the methods of the present invention to optimize therapeutic efficacy and/or reduce toxicity. In particular, the methods of the present invention provide algorithms useful for determining whether a subsequent dose of a tyrosine kinase inhibitor should be increased or decreased in order to reach a therapeutic threshold and/or minimize toxicity (e.g., side-effects). The methods of the present invention also provide algorithms useful for determining whether a suitable dose of an alternative cancer therapy should be administered due to the development of resistance to tyrosine kinase inhibitor therapy.

V. Profiles

The present invention provides assay methods for predicting, monitoring, or optimizing tyrosine kinase inhibitor therapy in a subject using an algorithmic approach by determining at least one nucleic acid and/or protein profile in a sample from the subject. Examples of nucleic acid profiles include, but are not limited to, a genotypic profile, gene copy number profile, gene expression profile, DNA methylation profile, and combinations thereof. Non-limiting examples of protein profiles include a protein expression profile, protein activation profile, and combinations thereof. Nucleic acid profiling typically comprises analyzing one or more genetic biomarkers, while protein profiling generally comprises analyzing one or more biochemical or serological biomarkers.

Several biomarkers may be combined into one test for efficient processing of multiple samples. In addition, one of skill in the art would recognize the value of testing multiple samples (e.g., at successive time points, before and after administration of a tyrosine kinase inhibitor, etc.) from the same subject. Such testing of serial samples can allow the identification of changes in biomarker levels over time. Increases or decreases in biomarker levels, as well as the absence of change in biomarker levels, can provide useful information to create a specific tyrosine kinase inhibitor dosing regimen for a subject diagnosed with cancer by determining the initial and/or subsequent doses of the drug that should be administered to the subject.

A panel consisting of one or more of the biomarkers described herein may be constructed to provide relevant information related to predicting, identifying, or monitoring efficacy and/or toxicity to tyrosine kinase inhibitor therapy. Such a panel may be constructed using 1, 2, 3, 4, 5, 6, 7, 8, 9, 10, 11, 12, 13, 14, 15, 16, 17, 18, 19, 20, 25, 30, 35, 40, 45, 50, or more individual biomarkers. The analysis of a single biomarker or subsets of biomarkers can also be carried out by one skilled in the art to optimize dose efficacy or reduce toxicity to tyrosine kinase inhibitor therapy in various clinical settings. These include, but are not limited to, ambulatory, urgent care, critical care, intensive care, monitoring unit, inpatient, outpatient, physician office, medical clinic, and health screening settings.

The analysis of biomarkers could be carried out in a variety of physical formats as well. For example, the use of microtiter plates or automation could be used to facilitate the processing of large numbers of test samples. Alternatively, single sample formats could be developed to facilitate diagnosis, prognosis, and/or treatment in a timely fashion.

A. Genotypic Profiling

A variety of techniques can be used for genotypic analysis of a polymorphic site in determining a genotypic profile according to the methods of the present invention. For example, enzymatic amplification of nucleic acid from a sample can be conveniently used to obtain nucleic acid for subsequent analysis. However, the presence or absence of a variant allele can also be determined directly from a nucleic acid sample without enzymatic amplification (e.g., using hybridization techniques). Genotyping of nucleic acid, whether amplified or not, can be performed using any of various techniques known to one of skill in the art. Useful techniques include, without limitation, polymerase chain reaction (PCR)-based analysis, sequence analysis, and electrophoretic analysis, which can be used alone or in combination.

A nucleic acid sample can be obtained from a subject using routine methods. Such samples comprise any biological matter from which nucleic acid can be prepared. As non-limiting examples, suitable samples include whole blood, serum, plasma, saliva, cheek swab, urine, or other bodily fluid or tissue that contains nucleic acid. In one embodiment, the methods of the present invention are performed using whole blood or fractions thereof such as serum or plasma, which can be obtained readily by non-invasive means and used to prepare genomic DNA. In another embodiment, genotyping involves the amplification of a subject's nucleic acid using PCR. Use of PCR for the amplification of nucleic acids is well known in the art (see, e.g., Mullis et al., *The Polymerase Chain Reaction*, Birkhäuser, Boston, (1994)). In yet another embodiment, PCR amplification is performed using one or more fluorescently labeled primers. In a further embodiment, PCR amplification is performed using one or more labeled or unlabeled primers containing a DNA minor grove binder. Generally, protocols for the use of PCR in identifying mutations and polymorphisms in a gene of interest are described in Theophilus et al., "PCR Mutation Detection Protocols," Humana Press (2002). Further protocols are provided in Innis et al., "PCR Applications: Protocols for Functional Genomics," 1st Edition, Academic Press (1999).

Any of a variety of different primers can be used to PCR amplify a subject's nucleic acid. One skilled in the art understands that primers for PCR analysis can be designed based on the sequence flanking the polymorphic site of interest. As a non-limiting example, a PCR primer can contain between about 15 to about 60 nucleotides (e.g., 15-50, 15-40, or 15-30 nucleotides) of a sequence upstream or downstream of the polymorphic site of interest. Such primers generally are designed to have sufficient guanine and cytosine content to attain a high melting temperature which allows for a stable annealing step in the amplification reaction. Several computer programs, such as Primer Select, are available to aid in the design of PCR primers.

Primer sequences and amplification protocols for evaluating EGFR (HER1/ErbB1) mutations are known to those in the art and have been published in, e.g., Lynch et al., *New Eng. J. Med.*, 350:2129-2139 (2004); Paez et al., *Science,* 304:1497-1500 (2004); Pao et al., *Proc. Natl. Acad. Sci.*, 101:13306-

13311 (2004); and Pao et al., *PLoS Med.,* 2:57-61 (2005). Preferably, the subject is genotyped to determine the presence or absence of an activating mutation (i.e., gain-of-function allele) in the tyrosine kinase domain of the EGFR gene. Such mutations include, but are not limited to, a T→G mutation at nucleotide 2573 in the EGFR gene, which results in a substitution of arginine for leucine at position 858 (L858R); a T→A mutation at nucleotide 2582 in the EGFR gene, which results in a substitution of glutamine for leucine at position 861 (L858Q); a G→T mutation at nucleotide 2155 in the EGFR gene, which results in a substitution of cysteine for glycine at position 719 (G719C); a deletion of nucleotides 2235-2249 in the EGFR gene, which results in an in-frame deletion of amino acids 746-750; a deletion of nucleotides 2240-2251 in the EGFR gene, which results in an in-frame deletion of amino acids 747-751 and the insertion of a serine; and a deletion of nucleotides 2240-2257 in the EGFR gene, which results in an in-frame deletion of amino acids 747-753 and the insertion of a serine. Other deletions, insertions, and/or single nucleotide substitutions in exons 18, 19, and/or 21 of the EGFR gene can also be determined according to the methods of the present invention. Alternatively, the subject can be genotyped to determine the presence or absence of a loss-of-function mutation in the EGFR gene.

Primer sequences and amplification protocols for evaluating K-Ras mutations are known to those in the art and have been published in, e.g., Pao et al., *PLoS Med.,* 2:57-61 (2005). Preferably, the subject is genotyped to determine the presence or absence of an activating mutation in the K-Ras gene. Such mutations include, but are not limited to, a G→T mutation at nucleotide 34 in the K-Ras gene, which results in a substitution of cysteine for glycine at position 12 (G12C); a G→T mutation at nucleotide 37 in the K-Ras gene, which results in a substitution of cysteine for glycine at position 13 (G13C); a G→A mutation at nucleotide 35 in the K-Ras gene, which results in a substitution of aspartic acid for glycine at position 12 (G12D); a G→A mutation at nucleotide 34 in the K-Ras gene, which results in a substitution of serine for glycine at position 12 (G12S); and a G→T mutation at nucleotide 35 in the K-Ras gene, which results in a substitution of valine for glycine at position 12 (G12V). Alternatively, the subject can be genotyped to determine the presence or absence of a loss-of-function mutation in the K-Ras gene.

Primer sequences and amplification protocols for evaluating c-KIT mutations are known to those in the art and have been published in, e.g., Corless et al., *J. Mol. Diagn.,* 6:366-70 (2004); Hirota et al., *Science,* 279:577-580 (1998); Hirota et al., *J. Pathol.,* 193:505-510 (2001); Antonescu et al., *Clin. Cancer Res.,* 9:3329-3337 (2003); Emile et al., *Diagn. Mol. Pathol.,* 11:107-112 (2002); Lasota et al., *Am. J. Pathol.,* 157:1091-1095 (2000); Lee et al., *Am. J. Surg. Pathol.,* 25:979-987 (2001); Lux et al, *Am. J. Pathol.,* 156:791-795 (2000); and Taniguchi et al., *Cancer Res.,* 59:4297-4300 (1999). Preferably, the subject is genotyped to determine the presence or absence of an activating mutation in the c-KIT gene. Such mutations include, but are not limited to, any of a variety of deletions, insertions, and/or single nucleotide substitutions in exons 9, 11, 13, and/or 17 of the c-KIT gene. Alternatively, the subject can be genotyped to determine the presence or absence of a loss-of-function mutation in the c-KIT gene.

Primer sequences and amplification protocols for evaluating PDGFRA mutations are known to those in the art and have been published in, e.g., Hirota et al, *Pathol. Int.,* 56:1-9 (2006); Corless et al., *J. Clin. Oncol.,* 23:5357-5364 (2005); and Penzel et al., *J. Clin. Pathol.,* 58:634-639 (2005). Preferably, the subject is genotyped to determine the presence or absence of an activating mutation in the PDGFRA gene. Such mutations include, but are not limited to, any of a variety of deletions, insertions, and/or single nucleotide substitutions in exons 12, 14, and/or 18 of the PDGFRA gene. Alternatively, the subject can be genotyped to determine the presence or absence of a loss-of-function mutation in the PDGFRA gene.

Primer sequences and amplification protocols for evaluating VEGFR-1 (FLT-1) mutations are known to those in the art and have been published in, e.g., Meshinchi et al., *Blood,* 102:1474-1479 (2003). Preferably, the subject is genotyped to determine the presence or absence of an activating mutation in the VEGFR-1 gene. Such mutations include, but are not limited to, any of a variety of deletions, insertions, and/or single nucleotide substitutions in the juxtamembrane domain or tyrosine kinase domain of the VEGFR-1 gene. Alternatively, the subject can be genotyped to determine the presence or absence of a loss-of-function mutation in the VEGFR-1 gene.

Primer sequences and amplification protocols for evaluating VEGFR-2 (FLK-1/KDR) mutations are known to those in the art and have been published in, e.g., Walter et al., *Genes Chromosomes Cancer,* 33:295-303 (2002); and Meshinchi et al., *Blood,* 102:1474-1479 (2003). Preferably, the subject is genotyped to determine the presence or absence of an activating mutation in the VEGFR-2 gene. Such mutations include, but are not limited to, any of a variety of deletions, insertions, and/or single nucleotide substitutions in the juxtamembrane domain or tyrosine kinase domain of the VEGFR-2 gene, such as a missense mutation (P1147S) in the kinase domain. Alternatively, the subject can be genotyped to determine the presence or absence of a loss-of-function mutation in the VEGFR-2 gene.

Primer sequences and amplification protocols for evaluating VEGFR-3 (FLT-4) mutations are known to those in the art and have been published in, e.g., Walter et al., *Genes Chromosomes Cancer,* 33:295-303 (2002). Preferably, the subject is genotyped to determine the presence or absence of an activating mutation in the VEGFR-3 gene. Such mutations include, but are not limited to, any of a variety of deletions, insertions, and/or single nucleotide substitutions in the juxtamembrane domain or tyrosine kinase domain of the VEGFR-3 gene, such as a missense mutation (P954S) in the kinase domain. Alternatively, the subject can be genotyped to determine the presence or absence of a loss-of-function mutation in the VEGFR-3 gene.

Primer sequences and amplification protocols for evaluating FLT-3 (FLK-2) mutations are known to those in the art and have been published in, e.g., Gilliland et al., *Curr. Opin., Hematol.,* 9:274-281 (2002); and Gilliland et al., *Blood,* 100: 1532-1542 (2002). Preferably, the subject is genotyped to determine the presence or absence of an activating mutation in the FLT-3 gene. Such mutations include, but are not limited to, an internal tandem duplication in the juxtamembrane domain of the FLT-3 gene; and an activating loop mutation in the tyrosine kinase domain of the FLT-3 gene, which results in a substitution of aspartic acid for another amino acid at position 835 (D835X). Alternatively, the subject can be genotyped to determine the presence or absence of a loss-of-function mutation in the FLT-3 gene.

A Taqman® allelic discrimination assay available from Applied Biosystems (Foster City, Calif.) can be useful for genotypic analysis of a polymorphic site to determine the presence or absence of a variant allele. In a Taqman® allelic discrimination assay, a specific, fluorescent dye-labeled probe for each allele is constructed. The probes contain different fluorescent reporter dyes such as FAM and VIC to differentiate the amplification of each allele. In addition, each probe has a quencher dye at one end which quenches fluorescence by fluorescence resonance energy transfer. During PCR, each probe anneals specifically to complementary sequences in the nucleic acid from the subject. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor grove binder (MGB) group to a DNA probe as described, e.g., in Kutyavin et al., *Nuc. Acids Res.*, 28:655-661 (2000). Suitable minor grove binders for use in the present invention include, but are not limited to, compounds such as dihydrocyclopyrroloindole tripeptide (DPI3).

Sequence analysis can also be useful for genotyping at a polymorphic site in a gene. In one embodiment, a variant allele can be detected by sequence analysis using the appropriate primers, which are designed based on the sequence flanking the polymorphic site of interest, as is known by those skilled in the art. As a non-limiting example, a sequencing primer can contain between about 15 to about 60 nucleotides (e.g., 15-50, 15-40, or 15-30 nucleotides) of a sequence between about 40 to about 400 base pairs upstream or downstream of the polymorphic site of interest. Such primers are generally designed to have sufficient guanine and cytosine content to attain a high melting temperature which allows for a stable annealing step in the sequencing reaction.

As used herein, the term "sequence analysis" includes any manual or automated process by which the order of nucleotides in a nucleic acid is determined. As an example, sequence analysis can be used to determine the nucleotide sequence of a sample of DNA. The term encompasses, without limitation, chemical and enzymatic methods such as dideoxy enzymatic methods including, for example, Maxam-Gilbert and Sanger sequencing as well as variations thereof. The term also encompasses, without limitation, capillary array DNA sequencing, which relies on capillary electrophoresis and laser-induced fluorescence detection and can be performed using instruments such as the MegaBACE 1000 or ABI 3700. As additional non-limiting examples, the term encompasses thermal cycle sequencing (Sears et al., *Biotechniques*, 13:626-633 (1992)); solid-phase sequencing (Zimmerman et al., *Methods Mol. Cell Biol.*, 3:39-42 (1992); and sequencing with mass spectrometry, such as matrix-assisted laser desorption/ionization time-of-flight mass spectrometry (MALDI-TOF MS; Fu et al, *Nature Biotech.*, 16:381-384 (1998)). The term further includes, without limitation, sequencing by hybridization (SBH), which relies on an array of all possible short oligonucleotides to identify a segment of sequence (Chee et al., *Science*, 274:610-614 (1996); Drmanac et al., *Science*, 260:1649-1652 (1993); Drmanac et al., *Nature Biotech.*, 16:54-58 (1998)). One skilled in the art understands that these and additional variations are encompassed by the term as defined herein. See, in general, Ausubel et al., *Current Protocols in Molecular Biology*, Chapter 7 and Supplement 47, John Wiley & Sons, Inc., New York (1999).

In addition, electrophoretic analysis can be useful for genotyping at a polymorphic site in a gene. The term "electrophoretic analysis," as used herein in reference to one or more nucleic acids such as amplified fragments, includes a process whereby charged molecules are moved through a stationary medium under the influence of an electric field. Electrophoretic migration separates nucleic acids primarily on the basis of their charge, which is in proportion to their size, with smaller molecules migrating more quickly. The term includes, without limitation, analysis using slab gel electrophoresis such as agarose or polyacrylamide gel electrophoresis, or capillary electrophoresis. Capillary electrophoretic analysis generally occurs inside a small-diameter quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs in length. Such methods of electrophoretic analysis, and variations thereof, are well known in the art, as described, for example, in Ausubel et al., *Current Protocols in Molecular Biology*, Chapter 2 and Supplement 45, John Wiley & Sons, Inc., New York (1999).

Restriction fragment length polymorphism (RFLP) analysis can also be useful for genotypic analysis of a polymorphic site in a gene (see, e.g., Jarcho et al., *Current Protocols in Human Genetics*, pages 2.7.1-2.7.5, John Wiley & Sons, Inc., New York; Innis et al., *PCR Protocols*, San Diego, Academic Press, Inc. (1990)). As used herein, "restriction fragment length polymorphism analysis" includes any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

Furthermore, allele-specific oligonucleotide hybridization can be useful for genotyping at a polymorphic site in a gene. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele can also be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., *The Polymerase Chain Reaction*, Birkhäuser, Boston, (1994)). One skilled in the art understands that the one or more nucleotide mismatches that distinguish between the variant allele and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant allele and other alleles at the 3' end of the primer.

A heteroduplex mobility assay (HMA) is another well-known assay that can be used for genotyping at a polymorphic site in a gene. HMA is useful for detecting the presence of a variant allele since a DNA duplex carrying a mismatch has reduced mobility in a polyacrylamide gel compared to the mobility of a perfectly base-paired duplex (see, e.g., Delwart et al., *Science*, 262:1257-1261 (1993); White et al., *Genomics*, 12:301-306 (1992)).

The technique of single strand conformational polymorphism (SSCP) can also be useful for genotypic analysis of a polymorphic site in a gene according to the methods of the present invention (see, e.g., Hayashi, *Methods Applic.*, 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) is another useful technique for genotyping at a polymorphic site in a gene. In DGGE, double-stranded DNA is electrophoresed in a gel containing an increasing concentration of denaturant. Because double-stranded fragments comprising mismatched alleles have segments that melt more rapidly, such fragments migrate differently as compared to perfectly complementary sequences (Sheffield et al., "Identifying DNA Polymorphisms by Denaturing Gradient Gel Electrophoresis," in Innis et al., *PCR Protocols*, San Diego, Academic Press, Inc. (1990)).

Other molecular techniques useful for genotypic analysis of a polymorphic site in a gene are also known in the art and useful in the methods of the present invention. Other well-known genotyping techniques include, without limitation, automated sequencing and RNAase mismatch techniques (Winter et al., *Proc. Natl. Acad. Sci.*, 82:7575-7579 (1985)). Furthermore, one skilled in the art understands that, where the presence or absence of multiple variant alleles is to be determined, individual variant alleles can be detected by any combination of molecular techniques. See, in general, Birren et al., *Genome Analysis: A Laboratory Manual*, Volume 1 (Analyzing DNA), New York, Cold Spring Harbor Laboratory Press (1997). In addition, one skilled in the art understands that multiple variant alleles can be detected in individual reactions or in a single reaction, e.g., using a multiplex real-time PCR assay. Kits for performing multiplex real-time PCR of cDNA or genomic DNA targets using sequence-specific probes are available from QIAGEN Inc. (Valencia, Calif.), e.g., the QuantiTect Multiplex PCR Kit. Systems for performing multiplex real-time PCR are available from Applied Biosystems (Foster City, Calif.), e.g., the 7300 or 7500 Real-Time PCR Systems.

In view of the above, one skilled in the art will readily appreciate that the methods of the present invention for determining a genotypic profile in a sample can be practiced using one or any combination of the well-known techniques described above or other techniques known in the art.

B. Gene Expression Profiling

A gene expression profile is typically evaluated in vitro on a sample collected from a subject in comparison to a normal or reference sample. Determination of a transcriptional expression profile can be accomplished, e.g., using hybridization techniques well-known to those skilled in the art such as Northern analysis and slot blot hybridization or by performing reverse-transcriptase (RT)-PCR amplification followed by gel electrophoresis. Applicable PCR amplification techniques are described in Ausubel et al., *Current Protocols in Molecular Biology*, John Wiley & Sons, Inc., New York (1999); Theophilus et al., "PCR Mutation Detection Protocols," Humana Press (2002); and Innis et al., "PCR Applications: Protocols for Functional Genomics," 1st Edition, Academic Press (1999). General nucleic acid hybridization methods are described in Anderson, "Nucleic Acid Hybridization," BIOS Scientific Publishers (1999). Amplification or hybridization of a plurality of transcribed nucleic acid sequences (e.g., mRNA or cDNA) can also be performed using mRNA or cDNA sequences arranged in a microarray. Microarray methods are generally described in Hardiman, "Microarrays Methods and Applications: Nuts & Bolts," DNA Press (2003) and Baldi et al., "DNA Microarrays and Gene Expression: From Experiments to Data Analysis and Modeling," Cambridge University Press (2002).

Comparing patterns of gene expression is a widely used means of identifying novel genes, investigating gene function, and finding potential new therapeutic targets (Shiue et al., *Drug Devel. Res.*, 41:142-159 (1997)). Many techniques have been used to identify and clone differentially expressed genes (Liang et al., *Science*, 257:967-971 (1992); Welsh et al., *Nucleic Acids Res.*, 20:4965-4970 (1992); Tedder et al., *Proc. Natl. Acad. Sci.*, 85:208-212 (1988); Davis et al., *Proc. Natl. Acad. Sci.*, 81:2194-2198 (1984); Lisitsyn et al., *Science*, 259:946-951 (1993); Velculescu et al., *Science*, 270:484-487 (1995); Diatchenko et al., *Proc. Natl. Acad. Sci.*, 93:6025-6030 (1996); Jiang et al., *Proc. Natl. Acad. Sci.*, 97:12684-12689 (2000); Yang et al., *Nucleic Acids Res.*, 27: 517-523 (1999)).

Recently, it has become routine to use the technique of cDNA microarray hybridization to quantify the expression of many thousands of discrete mRNA or cDNA sequences in a single assay known as expression profiling (van't Veer et al., *Nature*, 415:530-536 (2002); Hughes et al., *Nature Biotech.*, 19:342-347 (2001); Hughes et al., *Cell*, 102:109-126 (2000); Lockhart and Winzeler, *Nature*, 405:827-836 (2000); Roberts et al., *Science*, 287:873-880 (2000); Wang et al., *Gene*, 229: 101-108 (1999); Lockhart et al., *Nat. Biotech.*, 14:1675-1680 (1996); Schena et al., *Science*, 270:467-470 (1995); U.S. Pat. No. 6,040,138). For example, EGFR mRNA levels can be measured in tumor samples by microarray hybridization as described in Bhargava et al., *Mod. Pathol.*, 18:1027-1033 (2005). In certain embodiments, a gene expression microarray groups genes according to similarities in patterns of gene expression in expression profiling experiments.

In addition, gene expression profiles can be used to identify pathway-specific reporters and target genes for a particular biological pathway of interest. Such reporter genes and probes directed to them can be used to measure the activity of a particular biological pathway and may be further used in the design of drugs, drug therapies, or other biological agents to target a particular biological pathway. Gene expression profiles can also be used to determine protein activity levels of a target protein using the methods described in U.S. Pat. No. 6,324,479.

The measurement of gene expression profiles using microarrays also has many important applications to the monitoring of disease states and therapies (see, e.g., U.S. Pat. Nos. 6,218,122 and 6,222,093), the identification of drug targets, the identification of pathways of drug action, and drug design (see, e.g., U.S. Pat. Nos. 6,303,291, 6,165,709, 6,146, 830, 5,965,352, and 5,777,888). For example, van't Veer et al., supra, identified "good prognosis" and "poor prognosis" gene expression signatures that could be used to predict the clinical outcome of breast cancer patients. Similarly, U.S. Pat. No. 5,777,888 discloses the utility of microarray gene expression profiles to evaluate the target specificity of a candidate drug by comparison of an expression profile obtained from cells treated with the candidate drug to a database of expression profiles obtained from cells treated with known drugs. U.S. Pat. No. 6,218,122 provides methods for monitoring the disease state of a subject and determining the effect of a therapy upon the subject through the use of gene expression profiles (see, also, U.S. Pat. No. 6,266,093). In addition, Shoemaker et al., *Nature*, 409:922-927 (2000), discloses methods for using microarray gene expression profiles to detect splice variants.

In view of the above, one skilled in the art will readily appreciate that the methods of the present invention for determining a gene expression profile from a sample of a subject can be practiced using one or any combination of the well-known techniques described above or other techniques known in the art.

C. Gene Copy Number Profiling

Analysis of biomarker gene amplification levels can also be used alone or in combination with other markers to predict, monitor, or optimize tyrosine kinase inhibitor therapy in a subject. Any method known in the art for detecting or determining a level of gene amplification of one or more of the biomarkers described herein is suitable for use in the present invention.

In some embodiments, the level of gene amplification of a biomarker can be determined by DNA-based techniques such as PCR or Southern blot analysis or by molecular cytogenetic techniques such as fluorescence in situ hybridization (FISH), chromogenic in situ hybridization (CISH), and immunohistochemistry (IHC). For example, the level of EGFR gene amplification in cancer cells can be determined using FISH as described in Cappuzzo et al., *J. Natl. Caner Inst.*, 97:643-655 (2005). Similarly, the level of HER2 gene amplification in cancer cells can be determined using FISH as described in Cappuzzo et al., *J. Clin. Oncol.*, 23:5007-5018 (2005). Likewise, the level of c-KIT, PDGFRA, and/or VEGFR2 gene amplification in cancer cells can be determined using FISH as described in Joensuu et al., *J. Pathol.*, 207:224-231 (2005). EGFR gene copy number can also be determined using real-time quantitative PCR as described in Bell et al., *J. Clin. Oncol.*, 23:8081-8092 (2005) or CISH as described in Bhargava et al., *Mod. Pathol.*, 18:1027-1033 (2005). Other techniques include genome-wide scanning of amplified chromosomal regions with comparative genomic hybridization for the detection of amplified regions in tumor DNA (see, e.g., Kallioniemi et al., *Science*, 258:818-821 (1992)) and the detection of gene amplification by genomic hybridization to cDNA microarrays (see, e.g., Heiskanen et al., *Cancer Res.*, 60:799-802 (2000)). One skilled in the art will know of additional gene amplification techniques that can be used to detect or determine a level of an amplified gene that corresponds to a biomarker of the present invention.

D. DNA Methylation Profiling

Analysis of biomarker DNA methylation levels can also be used alone or in combination with other markers to predict, monitor, or optimize tyrosine kinase inhibitor therapy in a subject.

The regulation of gene expression by epigenetic mechanisms such as methylation contributes to various biological processes including genomic imprinting, X-chromosomal inactivation, cellular differentiation, and aging, as well as the development of malignant diseases such as cancer (see, e.g., Ferguson-Smith et al., *Science*, 293:1086-1089 (2001); Lee, *Curr. Biol.*, 13:R242-254 (2003); Issa, *Clin. Immunol.*, 109: 103-108 (2003); and Robertson, *Nat. Rev. Genet.*, 6:597-610 (2005)). In mammals, methylation of DNA typically occurs at specific cytosine residues which precede a guanosine residue (i.e., CpG dinucleotides) and generally correlates with stable transcriptional repression (see, e.g., Bestor, *Hum. Mol. Genet.*, 9:2395-2402 (2000); Ng et al., *Curr. Opin. Genet. Dev.*, 9:158-163 (1999); and Razin, *EMBO J.*, 17, 4905-4908 (1998)). The aberrant gain of DNA methylation (i.e., hypermethylation) in neoplastic cells frequently affects DNA sequences with a relatively high content of CpG dinucleotides, known as CpG islands. These regions often contain transcription initiation sites and promoters and are generally not methylated in normal cells (see, e.g., Costello et al., *J. Med. Genet.*, 38:285-303 (2001); Tycko, *Mutat. Res.*, 386: 131-140 (1997); and Wolffe et al., *Proc. Natl Acad. Sci. USA*, 96:5894-5896 (1999)). However, hypermethylation of CpG islands causes transcriptional repression and, in cancer, leads to the abnormal silencing of genes such as tumor suppressor genes (see, e.g., Esteller et al., *Science*, 297:1807-1808 (2002); Herman et al., *N. Engl. J. Med.*, 349:2042-2054 (2003); Momparler, *Oncogene*, 22:6479-6483 (2003); and Plass, *Hum. Mol. Genet.*, 11:2479-2488 (2002)). As a result, analyzing the level of DNA methylation in, e.g., the genomic regulatory sequences of biomarkers such as tumor suppressor genes (e.g., PTEN, DMBT1, LGI1, p53, ESR1, CDKN2B, ICSBP, ETV3, DDX20, etc.) can be useful in the methods of the present invention.

Any technique known in the art can be used for detecting or determining the CpG methylation state of one or more of the biomarkers described herein. For example, the level of DNA methylation of a biomarker can be determined by chromatographic separation, use of methylation-sensitive restriction enzymes, and bisulfite-driven conversion of non-methylated cytosine to uracil (see, e.g., Ushijima, *Nat. Rev. Cancer*, 5:223-231 (2005)). Biomarker DNA methylation levels can also be determined by a system designed for the application of immunofluorescence using a monoclonal antibody that specifically recognizes 5'-methyl-cytosine residues in single-stranded DNA hybridized to oligonucleotide microarrays (see, e.g., Pröll et al., *DNA Res.*, 13:37-42 (2006)). Alternatively, the level of DNA methylation of a biomarker can be determined using the methyl-binding PCR technique described in Gebhard et al., *Nuc. Acids Res.*, 34:e82 (2006). One skilled in the art will know of additional techniques that can be used to detect or determine a level of methylation in the genomic regulatory sequences of the biomarkers described herein.

E. Protein Expression Profiling

A variety of techniques can be used to detect the presence or level of an expressed protein for determining a protein expression profile according to the methods of the present invention. For example, a proteinaceous biomarker can be analyzed using an immunoassay. A protein expression profile can also be evaluated using electrophoresis, e.g., Western blotting, as well as any other technique known to those skilled in the art. Immunoassay techniques and protocols are generally described in Price and Newman, "Principles and Practice of Immunoassay," 2nd Edition, Grove's Dictionaries (1997); and Gosling, "Immunoassays: A Practical Approach," Oxford University Press (2000). The presence or amount of the proteinaceous biomarker is typically determined using antibodies specific for the biomarker and detecting specific binding. For example, a monoclonal antibody directed to EGFR can be obtained from Zymed Laboratories (San Francisco, Calif.) and a monoclonal antibody directed to TGF-α can be obtained from Oncogene Science (Manhasset, N.Y.). Antibodies directed to other antigens of interest such as receptor tyrosine kinases (e.g., EGFR, HER2, ErbB3, ErbB4, c-KIT, PDGFA, PDGFB, FLT-3/FLK-2, FLK-1, FLT-1, FLT-4, ROS, ALK, LTK, RET, etc.), tumor suppressors (e.g., PTEN, DMBT1, LGI1, p53, etc.), and growth factors (e.g., TGF-α, EGF, HB-EGF, VEGF, PDGF, FGF, etc.) can be obtained from Santa Cruz Biotechnology (Santa Cruz, Calif.).

Any suitable immunoassay can be utilized for determining the presence of level of one or more proteinaceous biomarkers in a sample. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Preferably, the expression level of proteins such as EGFR and TGF-α are determined using an enzyme immunoassay such as ELISA. For example, TGF-α concentration in serum or plasma can be measured using an ELISA kit available from R&D Systems (Minneapolis, Minn.), and EGFR levels can be determined using an ELISA kit from Biosource International (Camarillo, Calif.) or Calbiochem (San Diego, Calif.).

Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody to the proteinaceous biomarker can be detected directly or indirectly. Direct labels include fluorescent or luminescent tags, metals, dyes, radionuclides, and the like, attached to the antibody. An antibody labeled with iodine-125 ($^{125}$I) can be used for determining the level of one or more biomarkers in a sample. A chemiluminescence assay using a chemiluminescent antibody specific for the biomarker is suitable for sensitive, non-radioactive detection of biomarker levels. An antibody labeled with fluorochrome is also suitable for determining the level of one or more biomarkers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Antigen capture assays can be useful in the methods of the present invention. For example, in an antigen capture assay, an antibody directed to a proteinaceous biomarker of interest is bound to a solid phase and sample is added such that the biomarker is bound by the antibody. After unbound proteins are removed by washing, the amount of bound marker can be quantitated using, for example, a radioimmunoassay (see, e.g., Harlow and Lane, Antibodies: A Laboratory Manual, Cold Spring Harbor Laboratory, New York (1988)). Sandwich enzyme immunoassays can also be useful in the methods of the present invention. For example, in a two-antibody sandwich assay, a first antibody is bound to a solid support, and the biomarker is allowed to bind to the first antibody. The amount of the biomarker is quantitated by measuring the amount of a second antibody that binds the biomarker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Quantitative Western blotting also can be used to detect or determine the level of one or more proteinaceous biomarkers in a sample. Western blots can be quantitated by well-known methods such as scanning densitometry or phosphorimaging. In certain instances, autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, e.g., in Parra et al., *J. Vasc. Surg.*, 28:669-675 (1998).

Alternatively, a variety of immunohistochemistry (IHC) techniques can be used to determine the level of one or more proteinaceous biomarkers in a sample. As used herein, the term "immunohistochemistry" or "IHC" encompasses techniques that utilize the visual detection of fluorescent dyes or enzymes coupled (i.e., conjugated) to antibodies that react with the biomarker using fluorescent microscopy or light microscopy and includes, without limitation, direct fluorescent antibody, indirect fluorescent antibody (IFA), anti-complement immunofluorescence, avidin-biotin immunofluorescence, and immunoperoxidase assays. An IFA assay, for example, is useful for determining whether a sample is positive for a particular marker of interest, the level of that marker, and/or the staining pattern of that marker. The concentration of the marker in a sample can be quantitated, e.g., through endpoint titration or through measuring the visual intensity of fluorescence compared to a known reference standard.

Any IHC technique known to one of skill in the art is suitable for use in the assay methods of the present invention. As a non-limiting example, IHC can be performed according to the following protocol: (1) slides containing the sample (e.g., tumor tissue) are deparaffinized with xylene/70% ethanol into phosphate buffered saline (PBS) at pH 7.4; (2) the slides are then immersed in 10 mM citric acid at pH 6.0, microwaved for about 37 minutes, and cooled down at room temperature (RT) for about 30-60 minutes; (3) endogenous peroxidases are quenched for about 10 minutes in 1 part 30% $H_2O_2$ and 9 parts methanol and the slides are washed 3 times for 3 minutes in PBS; (4) the slides are blocked with blocking reagent at RT for about 30 minutes; (5) antibodies against the biomarker of interest are added and the slides are incubated at 4° C. overnight; (6) the slides are washed in PBS at RT for about 30 minutes, changing the wash buffer every 5 minutes; (7) secondary antibodies such as biotinylated antibodies are added and the slides are incubated at RT for about 60 minutes; (8) the slides are washed in PBS at RT for about 30 minutes, changing the wash buffer every 5 minutes; (9) streptavidin is added and the slides are incubated at RT for about 30 minutes; (10) 3,3'-diaminobenzidine (DAB) is added, the slides are incubated for 5 minutes, the DAB is neutralized with bleach, and the slides are washed for 5 minutes with water; (11) the slides are counterstained with methylgreen for 3 minutes and washed 3 times with water; (12) the slides are dipped in 95% ethanol, followed by a 100% ethanol and xylene series; and (13) a coverslip is placed onto the slide.

Examples of IHC protocols for determining the presence or level of specific antigens of interest are known in the art. These include the IHC protocols described in, e.g., Ishikawa et al., *Cancer Res.*, 65:9176-9184 (2005) for TGF-α and amphiregulin; Cappuzzo et al., *J. Clin. Oncol.*, 23:5007-5018 (2005) for HER2; Cappuzzo et al., *J. Natl. Caner Inst.*, 97:643-655 (2005) for EGFR; Abrams et al., *Mol. Cancer Ther.*, 2:471-478 (2003) for c-KIT and PDGFRB; and Lee et al., *Anal. Quant. Cytol. Histol.*, 27:202-210 (2005) for PTEN. Tissue staining can be visualized using peroxidase-based immunostaining kits available from Vector Laboratories (Burlingame, Calif.) and DAKO (Glostrup, Denmark).

The presence or level of a proteinaceous biomarker can also be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a biomarker can also be determined by well-known methods including, without limitation, Bradford assays, Coomassie blue staining, silver staining, assays for radiolabeled protein, and mass spectrometry.

The analysis of a plurality of proteinaceous biomarkers may be carried out separately or simultaneously with one test sample. For separate or sequential assay of biomarkers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of biomarkers on a single surface. Particularly useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more biomarkers for detection at each location. Surfaces may alternatively comprise one or more discrete particles (e.g., microparticles or nanoparticles) immobilized at discrete locations of a surface, where the microparticles comprise antibodies to immobilize one or more biomarkers for detection.

In view of the above, one skilled in the art will readily appreciate that the methods of the present invention for determining a protein expression profile from a sample of a subject can be practiced using one or any combination of the well-known techniques described above or other techniques known in the art.

F. Protein Activation Profiling

Analysis of the activation or inhibition of proteinaceous biomarkers of interest can be used alone or in combination with other markers to predict, monitor, or optimize tyrosine kinase inhibitor therapy in a subject according to the methods of the present invention. Any method known in the art for detecting or determining the activity or activation state of one or more of the biomarkers described herein is suitable for use in the present invention.

In some embodiments, the activation or inhibition of a proteinaceous biomarker can be determined by molecular cytogenetic techniques such as immunohistochemistry (IHC). An IHC assay is particularly useful for determining the phosphorylation state of proteins that are activated or inhibited by phosphorylation at specific tyrosine, serine, and/or threonine residues. In particular, IHC can be performed to determine whether a sample is positive for a particular phosphorylated marker of interest, the level of that phosphorylated marker, and/or the staining pattern of that phosphorylated marker. As a non-limiting example, paraffin-embedded tumor tissue sections can be stained with antibodies against phospho-Akt (P-Akt) and phospho-MAPK (P-MAPK) as described in Cappuzzo et al., *J. Natl. Caner Inst.*, 96:1133-1141 (2004) to determine their activation state. Negative to weak P-MAPK staining typically indicates the absence of active MAPK, whereas moderate to strong staining generally indicates the presence of active MAPK. Since activation of Akt by phosphorylation results in the translocation of P-Akt from the cytoplasm to the nucleus, the presence of P-Akt staining in the nucleus indicates the presence of active Akt, whereas the absence of nuclear staining indicates the absence of active Akt. An additional IHC protocol for detecting P-Akt in tumor cells is described in Cappuzzo et al., *J. Natl. Caner Inst.*, 97:643-655 (2005).

Phospho-specific antibodies against various phosphorylated forms of proteins such as Akt, MAPK, EGFR, c-KIT, c-Src, FLK-1, PDGFRA, PDGFRB, PTEN, Raf, and MEK are available from Santa Cruz Biotechnology (Santa Cruz, Calif.). Such phospho-specific antibodies can also be used in techniques including any of the immunoassays described above (e.g., ELISA) as well as Western blotting and immunoprecipitation assays to determine the activation state of a protein of interest according to the methods of the present invention. For example, specific tyrosine phosphorylated forms of EGFR can be detected using EGFR Phospho ELISA kits available from Sigma-Aldrich (St. Louis, Mo.).

Other methods for detecting the phosphorylation state of a protein of interest include, but are not limited to, KIRA ELISA (see, e.g., U.S. Pat. Nos. 5,766,863; 5,891,650; 5,914, 237; 6,025,145; and 6,287,784), mass spectrometry (comparing size of phosphorylated and unphosphorylated protein), and the eTag™ assay system.

When at least one of the proteinaceous biomarkers of interest is an enzyme, a level of enzymatic activity can be determined to assess the activation state of the enzyme. For example, any of the receptor or non-receptor tyrosine kinases described herein can be assayed for the presence or level of kinase activity using an appropriate substrate. Similarly, any tyrosine or serine/threonine kinase or phosphatase involved in the downstream signaling of receptor tyrosine kinases can be assayed for the presence or level of kinase activity using a suitable substrate. Tyrosine kinase activity can be determined using kits available from Chemicon International, Inc. (Temecula, Calif.) and QIAGEN Inc. (Valencia, Calif.). A fluorescent-based tyrosine kinase or tyrosine phosphatase activity assay is available from Promega Corporation (Madison, Wis.) and is described in Goueli et al., *Cell Notes,* 8:15-20 (2004). The activity of serine/threonine kinases such as Akt and MAPK can be determined using a kit available from Stressgen Bioreagents (Victoria, BC, Canada) and Chemicon International, Inc., respectively.

In some embodiments, the activation state of interest corresponds to the phosphorylation state of a proteinaceous biomarker, the ubiquitination state of the biomarker, or the complexation state of the biomarker with another cellular molecule. Non-limiting examples of activation states (listed in parentheses) of tyrosine kinases and their signaling components that are suitable for detection include: EGFR (EGFRvIII, phosphorylated (p-) EGFR, EGFR:Shc, ubiquitinated (u-) EGFR, p-EGFRvIII); ErbB2 (p85:truncated (Tr)-ErbB2, p-ErbB2, p85:Tr-p-ErbB2, Her2:Shc, ErbB2:PI3K, ErbB2:EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); IGF-1R (p-IGF-1R, IGF-1R:IRS, IRS:PI3K, p-IRS, IGF-1R:PI3K); INSR (p-INSR); KIT (p-KIT); FLT3 (p-FLT3); HGFR1 (p-HGFR1); HGFR2 (p-HGFR2); RET (p-RET); PDGFRa (p-PDGFRa); PDGFRP (p-PDGFRP); VEGFR1 (p-VEGFR1, VEGFR1:PLCg, VEGFR1:Src); VEGFR2 (p-VEGFR2, VEGFR2:PLCy, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); Tie1 (p-Tie1); Tie2 (p-Tie2); EphA (p-EphA); EphB (p-EphB); NFKB and/or IKB (p-IK (S32), p-NFKB (5536), p-P65:IKBa); Akt (p-Akt (T308, 5473)); PTEN (p-PTEN); Bad (p-Bad (5112, S 136), Bad: 14-3-3); mTor (p-mTor (52448)); p70S6K (p-p70S6K (T229, T389)); Mek (p-Mek (5217, 5221)); Erk (p-Erk (T202, Y204)); Rsk-1 (p-Rsk-1 (T357, 5363)); Jnk (p-Jnk (T183, Y185)); P38 (p-P38 (T180, Y182)); Stat3 (p-Stat-3 (Y705, 5727)); Fak (p-Fak (Y576)); Rb (p-Rb (5249, T252, 5780)); Ki67; p53 (p-p53 (5392, S20)); CREB (p-CREB (5133)); c-Jun (p-c-Jun (S63)); cSrc (p-cSrc (Y416)); and paxillin (p-paxillin (Y118)).

Any method known in the art can be used to detect the complexation state of a proteinaceous biomarker of interest with another cellular molecule. Preferably, the formation of heterodimeric complexes between members of the EGFR family of receptor tyrosine kinases are detected in tumors or tumor cells. Several preferred methods are described below. These methods generally detect noncovalent protein-protein interactions between proteins of interest.

Immunoaffinity-based methods, such as immunoprecipitation or ELISA, can be used to detect heterodimeric complexes between proteins of interest (e.g., EGFR heterodimers). In one embodiment, antibodies against a particular EGFR subtype are used to immunoprecipitate complexes comprising that EGFR subtype from tumor cells, and the resulting immunoprecipitant is then probed for the presence of one or more additional EGFR subtypes by immunoblotting. In another embodiment, EGFR ligands specific to one or more types of EGFR heterodimers can be used to precipitate complexes, which are then probed for the presence of each EGFR subtype present in the complexes. In certain instances, the EGFR ligands can be conjugated to avidin and EGFR heterodimeric complexes purified on a biotin column.

In other embodiments, such as ELISA or antibody sandwich-type assays, antibodies against a particular EGFR subtype are immobilized on a solid support, contacted with tumor cells or tumor cell lysate, washed, and then exposed to antibodies against one or more additional EGFR subtypes. Binding of the latter antibody, which may be detected directly or by a secondary antibody conjugated to a detectable label, indicates the presence of EGFR heterodimers. In certain instances, EGFR ligands may be used in place of, or in combination with, antibodies against EGFR subtypes.

Immunoprecipitation with antibodies against EGFR subtypes can be followed by a functional assay for heterodimers, as an alternative or supplement to immunoblotting. In one embodiment, immunoprecipitation with antibodies against a particular EGFR subtype is followed by an assay for receptor tyrosine kinase activity in the immunoprecipitant. As a non-limiting example involving the detection of ErbB2:ErbB3 heterodimers, the presence of tyrosine kinase activity in the immunoprecipitant indicates that ErbB3 is most likely associated with ErbB2 because ErbB3 does not have intrinsic tyrosine kinase activity (see, e.g., Graus-Porta et al., *EMBO J.,* 16:1647-1655 (1997); Klapper et al., *Proc. Natl. Acad. Sci. USA,* 96:4995-5000 (1999)). As another non-limiting example involving the detection of ErbB2:EGFR heterodimers, immunoprecipitation with ErbB2 antibody can be followed by an assay for EGFR kinase activity. In this assay, the immunoprecipitant can be contacted with radioactive ATP and a peptide substrate that mimics the in vivo site of transphosphorylation of ErbB2 by EGFR. Phosphorylation of the peptide indicates co-immunoprecipitation and thus heterodimerization of EGFR with ErbB2. Receptor tyrosine kinase activity assays are well known in the art and include assays that detect phosphorylation of target substrates, for example, by phosphotyrosine antibody, and activation of cognate signal transduction pathways, such as the MAPK pathway.

Chemical or UV cross-linking can also be used to covalently join heterodimers on the surface of living tumor cells (see, e.g., Hunter et al., *Biochem. J.,* 320:847-853 (1996)). Examples of chemical cross-linkers include, but are not limited to, dithiobis(succinimidyl) propionate (DSP) and 3,3'-dithiobis(sulphosuccinim-idyl) propionate (DTSSP). In one embodiment, cell extracts from chemically cross-linked tumor cells are analyzed by SDS-PAGE and immunoblotted with antibodies to one or more antibodies against EGFR subtypes. A supershifted band of the appropriate molecular weight most likely represents specific EGFR heterodimers. This result may be confirmed by subsequent immunoblotting with the appropriate antibodies.

Fluorescence resonance energy transfer (FRET) can also be used to detect heterodimers between members of the EGFR family of receptor tyrosine kinases. FRET detects protein conformational changes and protein-protein interactions in vivo and in vitro based on the transfer of energy from a donor fluorophore to an acceptor fluorophore (see, e.g., Selvin, *Nat. Struct. Biol.,* 7:730-734 (2000)). Energy transfer takes place only if the donor fluorophore is in sufficient proximity to the acceptor fluorophore. In a typical FRET experiment, two proteins or two sites on a single protein are labeled with different fluorescent probes. One of the probes, the donor probe, is excited to a higher energy state by incident light of a specified wavelength. The donor probe then transmits its energy to the second probe, the acceptor probe, resulting in a reduction in the donor's fluorescence intensity and an increase in the acceptor's fluorescence emission. To measure the extent of energy transfer, the donor's intensity in a sample labeled with donor and acceptor probes is compared with its intensity in a sample labeled with donor probe only. Optionally, acceptor intensity is compared in donor/acceptor and acceptor only samples. Suitable probes are known in the art and include, for example, membrane permeant dyes (e.g., fluorescein, rhodamine, etc.), organic dyes (e.g., cyanine dyes, etc.), and lanthamide atoms. Methods and instrumentation for detecting and measuring energy transfer are known in the art.

FRET-based techniques suitable for detecting and measuring protein-protein interactions in individual cells are also known in the art. For example, donor photobleaching fluorescence resonance energy transfer (pbFRET) microscopy and fluorescence lifetime imaging microscopy (FLIM) may be used to detect the dimerization of cell surface receptors (see, e.g., Selvin, supra; Gadella et al., *J. Cell Biol.*, 129:1543-1558 (1995)). In one embodiment, pbFRET is used on cells either "in suspension" or "in situ" to detect and measure the formation of EGFR heterodimers, as described, e.g., in Nagy et al., *Cytometry*, 32:120-131 (1998). These techniques measure the reduction in a donor's fluorescence lifetime due to energy transfer. In a particular embodiment, a flow cytometric Foerster-type FRET technique (FCET) may be used to investigate EGFR heterodimerization, as described, e.g., in Nagy et al., supra, and Brockhoff et al., *Cytometry*, 44:33848 (2001).

FRET is preferably used in conjunction with standard immunohistochemical labeling techniques (see, e.g., Kenworthy, *Methods*, 24:289-296 (2001). For example, antibodies conjugated to suitable fluorescent dyes can be used as probes for labeling two different proteins. If the proteins are within proximity of one another, the fluorescent dyes act as donors and acceptors for FRET. Energy transfer can be detected by standard means. Energy transfer may be detected by flow cytometric means or by digital microscopy systems, such as confocal microscopy or wide-field fluorescence microscopy coupled to a charge-coupled device (CCD) camera.

In one embodiment of the present invention, antibodies against different EGFR subtypes are directly labeled with two different fluorophores. Tumor cells or tumor cell lysates are contacted with the differentially labeled antibodies, which act as donors and acceptors for FRET in the presence of particular EGFR heterodimers. Alternatively, unlabeled antibodies against the different EGFR subtypes are used along with differentially labeled secondary antibodies that serve as donors and acceptors. Energy transfer can be detected and the presence of EGFR heterodimers determined if the labels are found to be in close proximity.

In another embodiment, the presence of EGFR heterodimers on the surface of tumor cells is demonstrated by co-localization of EGFR subtypes using standard direct or indirect immunofluorescence techniques and confocal laser scanning microscopy. Alternatively, laser scanning imaging (LSI) can be used to detect antibody binding and co-localization of EGFR subtypes in a high-throughput format, such as a microwell plate, as described, e.g., in Zuck et al., *Proc. Natl. Acad. Sci. USA*, 96:11122-11127 (1999).

In further embodiments, the presence of EGFR heterodimers is determined by identifying enzymatic activity that is dependent upon the proximity of the heterodimer components. Antibodies against an EGFR subtype are conjugated with one enzyme and antibodies against another EGFR subtype are conjugated with a second enzyme. A first substrate for the first enzyme is added and the reaction produces a second substrate for the second enzyme. This leads to a reaction with another molecule to produce a detectable compound, such as a dye. The presence of another chemical breaks down the second substrate, so that reaction with the second enzyme is prevented unless the first and second enzymes, and thus the two antibodies, are in close proximity. In a particular embodiment, tumor cells or tumor cell lysates are contacted with an ErbB2 antibody that is conjugated with glucose oxidase and an ErbB3 or EGFR antibody that is conjugated with horseradish peroxidase. Glucose is added to the reaction, along with a dye precursor, such as DAB, and catalase. The presence of EGFR heterodimers is determined by the development of color upon staining for DAB.

Heterodimers may also be detected using methods based on the eTag™ assay system as described, e.g., in U.S. Pat. No. 6,673,550. An eTag™, or "electrophoretic tag," comprises a detectable reporter moiety, such as a fluorescent group. It may also comprise a "mobility modifier," which comprises a moiety having a unique electrophoretic mobility. These moieties allow for separation and detection of the eTag™ from a complex mixture under defined electrophoretic conditions, such as capillary electrophoresis (CE). The portion of the eTag™ containing the reporter moiety and, optionally, the mobility modifier is linked to a first target binding moiety by a cleavable linking group to produce a first binding compound. The first target binding moiety specifically recognizes a particular first target, such as a nucleic acid or protein. The first target binding moiety is not limited in any way, and may be, for example, a polynucleotide or a polypeptide. Preferably, the first target binding moiety is an antibody or antibody fragment. Alternatively, the first target binding moiety may be an EGFR ligand or binding-competent fragment thereof.

The linking group preferably comprises a cleavable moiety, such as an enzyme substrate, or any chemical bond that may be cleaved under defined conditions. When the first target binding moiety binds to its target, the cleaving agent is introduced and/or activated, and the linking group is cleaved, thus releasing the portion of the eTag™ containing the reporter moiety and mobility modifier. Thus, the presence of a "free" eTag™ indicates the binding of the target binding moiety to its target.

Preferably, a second binding compound comprises the cleaving agent and a second target binding moiety that specifically recognizes a second target. The second target binding moiety is also not limited in any way and may be, for example, an antibody or antibody fragment or an EGFR ligand or binding-competent fragment thereof. The cleaving agent is such that it will only cleave the linking group in the first binding compound If the first binding compound and the second binding compound are in close proximity.

As a non-limiting example, a first binding compound comprises an eTag™ in which antibodies against ErbB2 serve as the first target binding moiety. A second binding compound comprises antibodies against EGFR or ErbB3 joined to a cleaving agent capable of cleaving the linking group of the eTag™. Preferably, the cleaving agent must be activated in order to be able to cleave the linking group. Tumor cells or tumor cell lysates are contacted with the eTag™, which binds to ErbB2, and with the modified EGFR or ErbB3 antibodies, which binds to EGFR or ErbB3 on the cell surface. Unbound binding compound is preferably removed, and the cleaving agent is activated, if necessary. If EGFR:ErbB2 or ErbB2:ErbB3 heterodimers are present, the cleaving agent will cleave the linking group and release the eTag™ due to the proximity of the cleaving agent to the linking group. Free eTag™ may then be detected by any method known in the art, such as capillary electrophoresis. In certain instances, the cleaving agent is an activatable chemical species that acts on the linking group. For example, the cleaving agent may be activated by exposing the sample to light.

In view of the above, one skilled in the art will readily appreciate that the methods of the present invention for determining a protein activation profile from a sample of a subject can be practiced using one or any combination of the well-known techniques described above or other techniques known in the art.

VI. Selection of Antibodies

The generation and selection of antibodies not already commercially available for detecting or determining the level of proteinaceous biomarkers may be accomplished several ways. For example, one way is to purify polypeptides of interest or to synthesize the polypeptides of interest using, e.g., solid phase peptide synthesis methods well known in the art. See, e.g., *Guide to Protein Purification*, Murray P. Deutcher, ed., *Meth. Enzymol.*, Vol. 182, 1990; *Solid Phase Peptide Synthesis*, Greg B. Fields, ed., *Meth. Enzymol.*, Vol. 289, 1997; Kiso et al., *Chem. Pharm. Bull.*, 38:1192-99 (1990); Mostafavi et al., *Biomed. Pept. Proteins Nucleic Acids*, 1:255-60, (1995); Fujiwara et al., *Chem. Pharm. Bull.*, 44:1326-31 (1996). The selected polypeptides may then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic antibodies can also be prepared from genetic information by various procedures (see, e.g., *Antibody Engineering: A Practical Approach*, Borrebaeck, Ed., Oxford University Press, Oxford (1995); *J. Immunol.*, 149:3914-3920 (1992)).

In addition, numerous publications have reported the use of phage display technology to produce and screen libraries of polypeptides for binding to a selected target (see, e.g, Cwirla et al., *Proc. Natl. Acad. Sci. USA*, 87:6378-6382 (1990); Devlin et al., *Science*, 249:404-406 (1990); Scott et al., *Science*, 249:386-388 (1990); and Ladner et al., U.S. Pat. No. 5,571,698). A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means (see, e.g., U.S. Pat. No. 6,057, 098).

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or group of antibodies is then placed into the respective microtiter wells and incubated for about 30 min to 2 h. The microtiter wells are then washed and a labeled secondary antibody (e.g., an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide (s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ, certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the present invention.

VII. Algorithms

The present invention provides assay methods for predicting, monitoring, or optimizing tyrosine kinase inhibitor therapy in a subject using an algorithmic analysis of a panel of biomarkers in a sample from the subject. In particular, the algorithms described herein can advantageously provide improved sensitivity, specificity, negative predictive value, positive predictive value, and/or overall accuracy for carrying out the methods of the present invention.

The term "algorithm" includes any of a variety of statistical analyses used to determine relationships between variables. In some embodiments of the present invention, the variables are profiles such as nucleic acid and/or protein profiles. In these embodiments, the algorithm is used, e.g., to predict, identify, monitor, and/or optimize tyrosine kinase inhibitor efficacy, toxicity, and/or resistance in a tumor, tumor cell, or patient. Any number of profiles can be analyzed using an algorithm according to the methods of the present invention. For example, 1, 2, 3, 4, 5, 6, 7, 8, 9, 10, 11, 12, 13, 14, 15, 16, 17, 18, 19, 20, 25, 30, 35, 40, 45, 50, or more profiles can be included in an algorithm. In one embodiment, logistic regression is used. In another embodiment, linear regression is used. In certain instances, the algorithms of the present invention can use a quantile measurement of a particular profile within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into five groups containing (as far as possible) equal numbers of observations. The present invention can also include the use of percentile ranges of profiles (e.g., tertiles, quartile, quintiles, etc.), or their cumulative indices (e.g., quartile sums of profiles, etc.) as variables in the algorithms (just as with continuous variables).

As used herein, the term "index value" refers to a number for a subject that is determined using an algorithm according to the methods of the present invention. For example, the index value may be determined using logistic regression and correspond to a number between 0 and 1, e.g., 0.1, 0.2, 0.3, 0.4, 0.5, 0.6, 0.7, 0.8, 0.9, and further divisions thereof such as 0.25 or 0.225. Preferably, the index value is presented as a "cumulative index value," which represents a summation of those values determined from the assessment of at least one nucleic acid and/or protein profile (see, e.g., Examples 1 and 2 below). The cumulative index value can be compared to an index cut-off value, or the ratio of cumulative index values of all tested profiles can be divided by an index cut-off value, e.g., to predict, identify, monitor, and/or optimize tyrosine kinase inhibitor efficacy, toxicity, and/or resistance in a tumor, tumor cell, or patient.

The term "index cutoff value" refers to a number chosen on the basis of population analysis that is used for comparison to an index value calculated for a subject. Thus, the index cutoff value is based on analysis of index values determined using an algorithm. Those of skill in the art will recognize that an index cutoff value can be determined according to the needs of the user and characteristics of the analyzed population. When the algorithm is logistic regression, the index cutoff value will, of necessity, be between 0 and 1, e.g., between 0.1 to 0.9, 0.2 to 0.8, 0.3 to 0.7, or 0.4 to 0.6. Preferably, the index cutoff value is calculated according to the formulas set forth in Examples 1 and 2 below.

The term "iterative approach" refers to the analysis of at least one profile associated with cancer from a subject using more than one algorithm and/or index cutoff value. For example, two or more algorithms could be used to analyze different sets of profiles. As another example, a single algorithm could be used to analyze at least one profile, but more than one index cutoff value based on the algorithm could be used in the methods of the present invention.

In certain instances, cut-off values can be determined and independently adjusted for each of a number of biomarkers to observe the effects of the adjustments on clinical parameters such as sensitivity, specificity, negative predictive value, positive predictive value, and overall accuracy. In particular, Design of Experiments (DOE) methodology can be used to simultaneously vary the cut-off values and to determine the effects on the resulting clinical parameters of sensitivity, specificity, negative predictive value, positive predictive value, and overall accuracy. The DOE methodology is advantageous in that variables are tested in a nested array requiring fewer runs and cooperative interactions among the cut-off variables can be identified. Optimization software such as DOE Keep It Simple Statistically (KISS) can be obtained from Air Academy Associates (Colorado Springs, Colo.) and can be used to assign experimental runs and perform the simultaneous equation calculations. Using the DOE KISS program, an optimized set of cut-off values for a given clinical parameter and a given set of biomarkers can be calculated. ECHIP optimization software, available from ECHIP, Inc. (Hockessin, Del.), and Statgraphics optimization software, available from STSC, Inc. (Rockville, Md.), are also useful for determining cut-off values for a given set of biomarkers. Alternatively, cut-off values can be determined using Receiver Operating Characteristic (ROC) curves and adjusted to achieve the desired clinical parameter values.

In some embodiments, the algorithms of the present invention comprise one or more learning statistical classifier systems. As used herein, the term "learning statistical classifier system" refers to a machine learning algorithmic technique capable of adapting to complex data sets and making decisions based upon such data sets. In some embodiments, one or more learning statistical classifier systems are used, e.g., 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (CART), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning*, 45:5-32 (2001); and http://stat-www.berkeley.edu/users/breiman/RandomForests/cc_home.htm, for a description of random forests.

Classification and regression trees represent a computer intensive alternative to fitting classical regression models and are typically used to determine the best possible model for a categorical or continuous response of interest based upon one or more predictors. Classification and regression tree analysis can be performed, e.g., using the CART software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM-$^{light}$ software developed by Thorsten Joachims (Cornell University) or using the LIBSVM software developed by Chih-Chung Chang and Chih-Jen Lin (National Taiwan University).

The learning statistical classifier systems described herein can be trained and tested using a cohort of samples from healthy individuals, cancer patients, cancer cell lines, and the like. For example, samples from patients diagnosed by a physician, and preferably by an oncologist, as having cancer are suitable for use in training and testing the learning statistical classifier systems of the present invention. Samples from healthy individuals can include those that were not identified as having cancer. In certain embodiments, samples from cancer cell lines can be used in training and testing the learning statistical classifier systems described herein (see, e.g., Example 4 below). One skilled in the art will know of additional techniques and diagnostic criteria for obtaining a cohort of samples that can be used in training and testing the learning statistical classifier systems of the present invention.

As used herein, the term "sensitivity" refers to the probability that an algorithm of the present invention gives a positive result when the sample is positive. Sensitivity is calculated as the number of true positive results divided by the sum of the true positives and false negatives. Sensitivity essentially is a measure of how well an algorithm of the present invention correctly identifies responders (e.g., subjects likely to respond to tyrosine kinase inhibitor therapy, subjects without acquired resistance to tyrosine kinase inhibitor therapy, etc.) from non-responders. The marker values or learning statistical classifier models (e.g., random forest or neural network models) can be selected such that the sensitivity is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" as used herein refers to the probability that an algorithm of the present invention gives a negative result when the sample is not positive. Specificity is calculated as the number of true negative results divided by the sum of the true negatives and false positives. Specificity essentially is a measure of how well an algorithm of the present invention excludes non-responders from responders. The marker values or learning statistical classifier models can be selected such that the specificity is at least about 70%, for example, at least about 75%, 80%, 85%, 86%, 87%, 88%, 89%, 90%, 91%, 92%, 93%, 94%, 95%, 96%, 97%, 98%, or 99%.

As used herein, the term "negative predictive value" or "NPV" refers to the probability that a subject classified as a non-responder is actually unlikely to respond to tyrosine kinase inhibitor therapy or has developed acquired resistance to tyrosine kinase inhibitor therapy. Negative predictive value can be calculated as the number of true negatives divided by the sum of the true negatives and false negatives. Negative predictive value is determined by the characteristics of the algorithm as well as the prevalence of the disease in the population analyzed. The marker values or learning statistical classifier models can be selected such that the negative predictive value in a population having a disease prevalence is at least about 70% and can be, for example, at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" as used herein refers to the probability that an individual classified as a responder is actually likely to respond to tyrosine kinase inhibitor therapy or has not developed acquired resistance to tyrosine kinase inhibitor therapy. Positive predictive value can be calculated as the number of true positives divided by the sum of the true positives and false positives. Positive predictive value is determined by the characteristics of the algorithm as well as the prevalence of the disease in the population analyzed. The marker values or learning statistical classifier models can be selected such that the positive predictive value in a population having a disease prevalence is at least about 25% and can be, for example, at least about 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the algorithms of the present invention, the marker values or learning statistical classifier models can be selected to produce a desired clinical parameter for a clinical population with a particular cancer prevalence. For example, marker values or learning statistical classifier models can be selected for a cancer prevalence of at least about 1%, 5%, 10%, 15%, 20%, 25%, 30%, 35%, 40%, 45%, 50%, 55%, 60%, 65%, or 70%, which can be seen, e.g., in a clinician's office or a general practitioner's office.

As used herein, the term "overall accuracy" refers to the accuracy with which an algorithm of the present invention classifies responders and non-responders. Overall accuracy is calculated as the sum of the true positives and true negatives divided by the total number of sample results and is affected by the prevalence of the disease in the population analyzed. For example, the marker values or learning statistical classifier models can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 95%, 96%, 97%, 98%, or 99%.

VIII. Methods of Administration

According to the methods of the present invention, the compounds described herein (e.g., tyrosine kinase inhibitors such as gefitinib and sunitinib) are administered to a subject by any convenient means known in the art. The assay methods of the present invention can be used to optimize dosage of tyrosine kinase inhibitors in subjects who have not received any tyrosine kinase inhibitor therapy as well as subjects who are currently undergoing tyrosine kinase inhibitor therapy. The assay methods of the present invention can also be used to reduce toxicity to tyrosine kinase inhibitors in subjects who have not received any tyrosine kinase inhibitor therapy as well as subjects who are currently undergoing tyrosine kinase inhibitor therapy. One skilled in the art will appreciate that tyrosine kinase inhibitors can be administered alone or as part of a combined therapeutic approach with conventional chemotherapy, radiotherapy, hormonal therapy, immunotherapy, and/or surgery.

Tyrosine kinase inhibitors can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that a tyrosine kinase inhibitor is administered at the same time, just prior to, or just after the administration of a second drug (e.g., another tyrosine kinase inhibitor, a drug useful for reducing the side-effects associated with tyrosine kinase inhibitor therapy, a chemotherapeutic agent, a radiotherapeutic agent, a hormonal therapeutic agent, an immunotherapeutic agent, etc.).

As a non-limiting example, the tyrosine kinase inhibitors described herein can be co-administered with conventional chemotherapeutic agents including platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

The tyrosine kinase inhibitors described herein can also be co-administered with conventional hormonal therapaeutic agents including, but not limited to, steroids (e.g., dexamethasone), finasteride, aromatase inhibitors, tamoxifen, and gonadotropin-releasing hormone agonists (GnRH) such as goserelin.

Additionally, the tyrosine kinase inhibitors described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a farther embodiment, the tyrosine kinase inhibitors described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

A therapeutically effective amount of a tyrosine kinase inhibitor may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of a tyrosine kinase inhibitor calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the tyrosine kinase inhibitor.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a tyrosine kinase inhibitor, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. A tyrosine kinase inhibitor can also be formulated into a suppository disposed, for example, in a polyethylene glycol (PEG) carrier.

Liquid dosage forms can be prepared by dissolving or dispersing a tyrosine kinase inhibitor and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A tyrosine kinase inhibitor can also be formulated into a retention enema.

For topical administration, the therapeutically effective dose can be in the form of emulsions, lotions, gels, foams, creams, jellies, solutions, suspensions, ointments, and transdermal patches. For administration by inhalation, a tyrosine kinase inhibitor can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the levels of certain biomarkers can change based on the therapeutic effect of a treatment such as a tyrosine kinase inhibitor. The subject can be monitored to assess response and understand the effects of certain drugs or treatments in an individualized approach. Additionally, subjects who initially respond to a tyrosine kinase inhibitor may become refractory to the drug, indicating that these subjects have developed acquired resistance to the drug. These subjects can be discontinued on their current therapy and alternative treatments prescribed.

IX. Examples

The following examples are offered to illustrate, but not to limit, the claimed invention.

Example 1

Algorithm for Predicting Response to Gefitinib (Iressa®) Therapy

This example illustrates an algorithm that was developed to predict response to gefitinib therapy. In particular, a representative panel of genetic, serological, and biochemical tests was performed on tumor, plasma, and/or serum samples to calculate a cumulative index value for a subject diagnosed with a solid tumor such as non-small cell lung cancer. In this example, representative index values predictive of gefitinib sensitivity were assigned a value of 1. However, one skilled in the art will appreciate that the index values need not be integers. The final individual profile assessment can be presented as a cumulative index value, which represents a summation of the representative index values determined for each biomarker. In certain instances, one or more biomarkers can have a weighted representative index value.

As shown in FIG. 1, a subject diagnosed with a cancer such as non-small cell lung cancer is first genotyped at a polymorphic site in EGFR to determine the presence or absence of an EGFR activating mutation (100). The presence of an EGFR activating mutation indicates that administration of gefitinib should be recommended. Subjects who do not have an EGFR activating mutation are then genotyped at a polymorphic site in K-Ras to determine the presence or absence of a K-Ras activating mutation (110). The presence of a K-Ras activating mutation indicates that administration of another tyrosine kinase inhibitor or an alternative cancer therapy should be recommended. One skilled in the art will appreciate that genotyping K-Ras can be performed at the same time, just prior to, or just after genotyping EGFR.

Various nucleic acid and/or protein profiles are then determined for those subjects who do not have EGFR and K-Ras activating mutations using a panel of biomarkers (120). For example, a gene copy number profile can be determined by analyzing EGFR copy number and HER2 copy number; a protein expression profile can be determined by measuring EGFR expression, TGF-α expression, and PTEN expression; and a protein activation profile can be determined by assessing Erk (MAPK) activation and Akt activation. A cumulative index value (CIV) based upon the sum of the representative index values for each of these biomarkers can be calculated according to the following formula (130):

$$CIV = (2 \times EGFR \text{ copy number}) + (2 \times EGFR \text{ expression}) + Erk(MAPK) \text{activation} + Akt \text{ activation} + TGF\text{-}\alpha \text{ expression} + HER2 \text{ copy number} + PTEN \text{ expression},$$

wherein

| | | | Representative Index Values | |
|---|---|---|---|---|
| Marker | Sample | Assay | 0 | 1 |
| EGFR copy number | Tumor | FISH | No or low genomic gain | High polysomy or gene amplification |
| | Tumor | PCR | ≦4-fold amplification | >4-fold amplification |
| EGFR expression | Tumor | IHC | Negative to weak staining | Moderate to strong staining |
| | Serum/Plasma | ELISA | ≦850 ng/ml | >850 ng/ml |
| Erk (MAPK) activation | Tumor | IHC | Negative to weak staining | Moderate to strong staining |
| Akt activation | Tumor | IHC | Nuclear staining absent | Nuclear staining present |
| TGF-α expression | Tumor | IHC | Moderate to strong staining | Negative to weak staining |
| | Serum/Plasma | ELISA | >15 pg/ml | ≦15 pg/ml |
| HER2 copy number | Tumor | FISH | No or low genomic gain | High polysomy or gene amplification |
| PTEN expression | Tumor | IHC | Negative to weak staining | Moderate to strong staining |

Here, a cumulative index value greater than or equal to an index cut-off value of 4 is predictive of gefitinib sensitivity or an increased likelihood of responding to gefitinib (140). Administration of gefitinib should be recommended. However, a cumulative index value less than an index cut-off value of 4 is predictive of gefitinib insensitivity or a decreased likelihood of responding to gefitinib. Administration of another tyrosine kinase inhibitor or an alternative cancer therapy should be recommended.

Example 2

Algorithm for Predicting Response to Sunitinib (Sutent®) Therapy

This example illustrates an algorithm that was developed to predict response to sunitinib therapy. In particular, a representative panel of genetic, serological, and biochemical tests was performed on tumor, plasma, and/or serum samples to calculate a cumulative index value for a subject diagnosed with a solid tumor such as a gastrointestinal stromal tumor or renal cell carcinoma. In this example, representative index values predictive of sunitinib sensitivity were assigned a value of 1. However, one skilled in the art will appreciate that the index values need not be integers. The final individual profile assessment can be presented as a cumulative index value, which represents a summation of the representative index values determined for each biomarker. In certain instances, one or more biomarkers can have a weighted representative index value.

Figure 2:
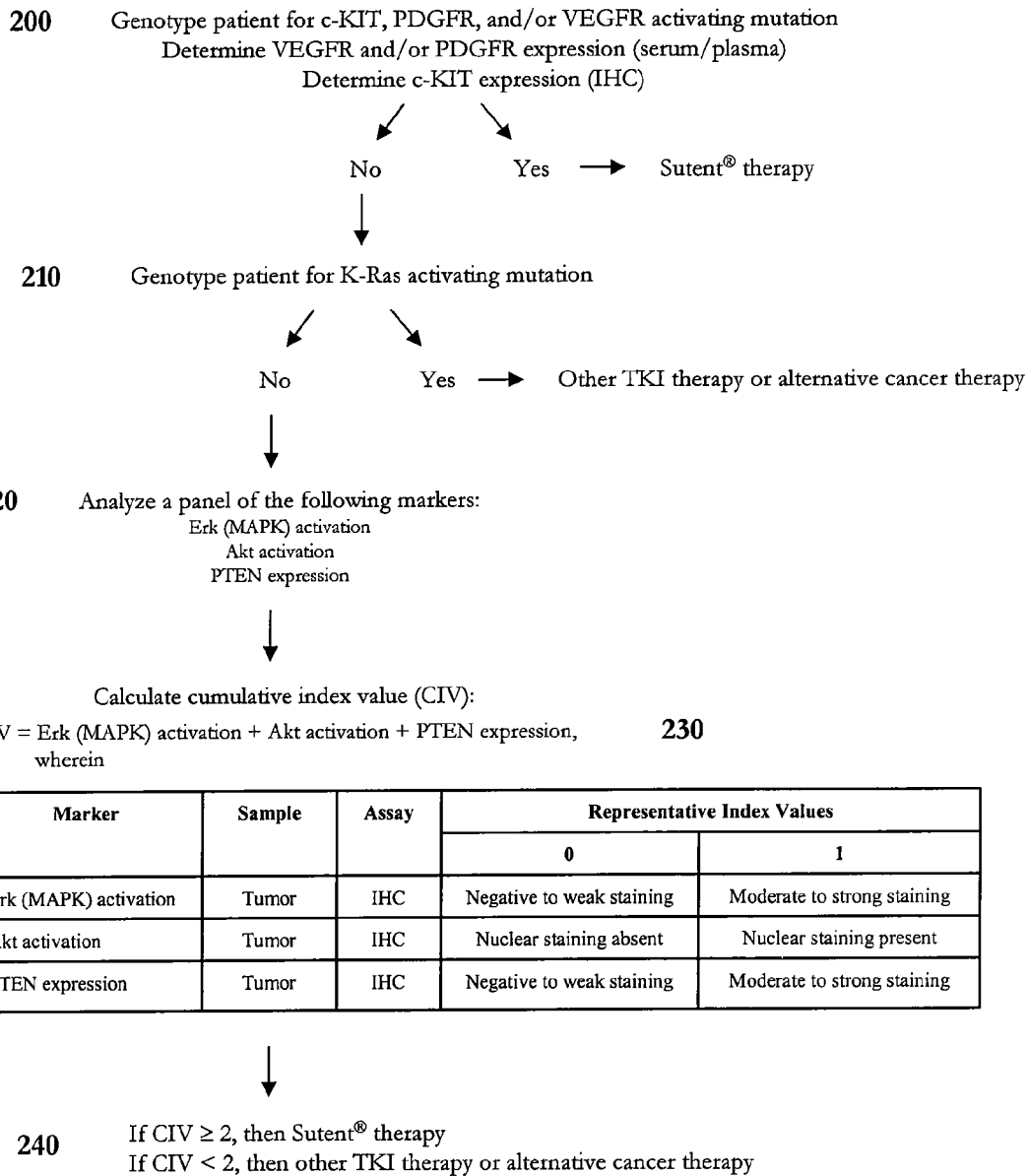
FIG. 2 shows a flowchart of another embodiment of the present invention describing an algorithm for individualizing sunitinib (Sutent®) therapy in patients with cancer.

As shown in FIG. 2, a subject diagnosed with a cancer such as a gastrointestinal stromal tumor or renal cell carcinoma is first genotyped at a polymorphic site in c-KIT, PDGFR, and/or VEGFR to determine the presence or absence of activating mutations in these genes (200). In addition, VEGFR and/or PDGFR expression is measured in a serum or plasma sample and c-KIT expression is determined by immunohistochemistry (IHC). The presence of a c-KIT, PDGFR, and/or VEGFR activating mutation, in combination with VEGFR and/or PDGFR overexpression and c-KIT overexpression, indicates that administration of sunitinib should be recommended. Subjects negative for these biomarkers are then genotyped at a polymorphic site in K-Ras to determine the presence or absence of a K-Ras activating mutation (210). The presence of a K-Ras activating mutation indicates that administration of another tyrosine kinase inhibitor or an alternative cancer therapy should be recommended. One skilled in the art will appreciate that genotyping K-Ras can be performed at the same time, just prior to, or just after genotyping c-KIT, PDGFR, and/or VEGFR.

Various nucleic acid and/or protein profiles are then determined for those subjects who are negative for c-KIT, PDGFR, VEGFR, and K-Ras activating mutations and do not overexpress VEGFR, PDGFR, and c-KIT using a panel of biomarkers (220). For example, a protein expression profile can be determined by measuring PTEN expression; and a protein activation profile can be determined by assessing Erk (MAPK) activation and Akt activation. A cumulative index value (CIV) based upon the sum of the representative index values for each of these biomarkers can be calculated according to the following formula (230):

$$CIV = Erk(MAPK)\text{activation} + Akt\text{ activation} + PTEN\text{ expression, wherein}$$

| | | | Representative Index Values | |
|---|---|---|---|---|
| Marker | Sample | Assay | 0 | 1 |
| Erk (MAPK) activation | Tumor | IHC | Negative to weak staining | Moderate to strong staining |
| Akt activation | Tumor | IHC | Nuclear staining absent | Nuclear staining present |
| PTEN expression | Tumor | IHC | Negative to weak staining | Moderate to strong staining |

Here, a cumulative index value greater than or equal to an index cut-off value of 2 is predictive of sunitinib sensitivity or an increased likelihood of responding to sunitinib (240). Administration of sunitinib should be recommended. However, a cumulative index value less than an index cut-off value of 2 is predictive of sunitinib insensitivity or a decreased likelihood of responding to sunitinib. Administration of another tyrosine kinase inhibitor or an alternative cancer therapy should be recommended.

Example 3

Biomarker Analysis in Fractionated Whole Blood

This example illustrates the use of fractionated whole blood for determining a spectrum of profiles including a genotypic profile, gene copy number profile, gene expression profile, DNA methylation profile, protein expression profile, protein activation profile, and combinations thereof. Whole blood which has been separated into its liquid and cellular components can also be used for determining the localization of proteinaceous biomarkers of interest, the morphology of cells of interest, and the number of circulating tumor and/or endothelial cells in a subject diagnosed with a solid tumor.

Figure 3:
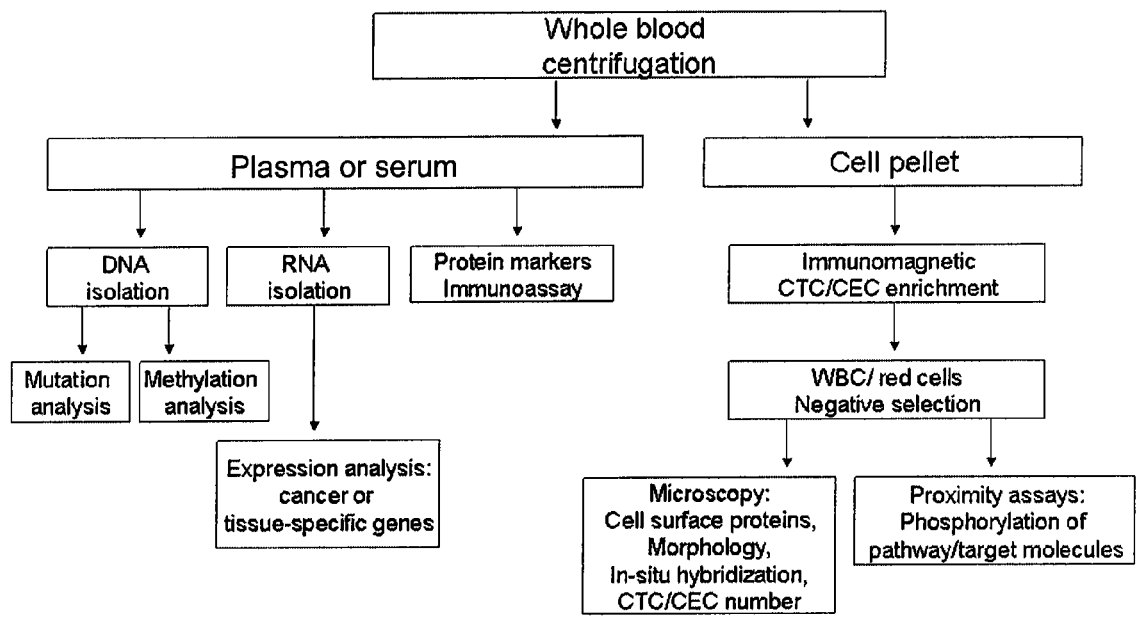
FIG. 3 shows a flow diagram illustrating the various analyses that can be performed on each whole blood fraction.

Circulating tumor and/or endothelial cells can act as a surrogate for biomarker analysis of the primary or metastatic tumor. In addition to releasing intact viable cells into the circulation, tumors also release freely circulating DNA, RNA, and shed proteins at levels that can be analyzed with current technologies. By segregating a whole blood sample into its fluid and cellular components, an entire spectrum of biomarkers can be analyzed using a single sample. As a result, all of the biomarkers in Examples 1 and 2 that are typically analyzed in tumor tissue can alternatively be analyzed in a fractional component of whole blood. FIG. 3 shows a flow diagram illustrating the analyses applicable for each whole blood fraction.

Whole blood is typically fractionated into a plasma or serum component and a cellular component using an art-recognized method such as centrifugation. As a non-limiting example, whole blood can be collected according to standard procedures in tubes containing an anticoagulant such as EDTA and fractionated by centrifuging at about 1500-2000×g for about 10-15 min at room temperature. This protocol is useful for separating whole blood into an upper plasma layer (i.e., plasma fraction) and a lower cellular layer (i.e., cell pellet fraction).

As shown in FIG. 3, DNA, RNA, and proteins secreted by tumor cells can be analyzed in the plasma fraction of whole blood. For example, DNA can be isolated from the plasma fraction using any method known in the art and a mutational analysis performed to determine the genotype of genes such as tyrosine kinase genes and/or a small GTPase genes. The level of DNA methylation in genomic regulatory sequences can also be detected in isolated DNA using any of the techniques described above. In addition, RNA can be isolated from the plasma fraction using any method known in the art and a gene expression analysis can be performed to determine the level of expression of cancer and/or tissue-specific genes using any of the above-described techniques. Moreover, the expression level of one or more proteinaceous biomarkers such as tyrosine kinases, growth factors, and/or tumor suppressors can be determined in a plasma fraction using immunoassays or other art-recognized techniques as described above.

FIG. 3 also shows that circulating tumor cells (CTCs) and circulating endothelial cells (CECs) can be analyzed in the cell pellet fraction of whole blood. Since CTCs and CECs are relatively rare, they can first be enriched using an immunomagnetic assay available from, e.g., Immunicon Corp. (Huntingdon Valley, Pa.), or any other magnetic-activated cell separation technique known in the art. A negative selection can also be performed to remove red blood cells and white blood cells from the cell pellet fraction. The enriched CTCs and CECs can be analyzed using any of a variety of microscopic techniques including, for example, in situ hybridization, immunohistochemistry, and immunofluorescence, to determine cell surface protein expression and/or localization, cell morphology, and CTC/CEC number. Proximity-based assays such as scintillation proximity assays (see, e.g., McDonald et al., *Anal. Biochem.*, 268:318-329 (1999), fluorescence polarization assays (see, e.g., Scott et al., *Anal. Biochem.*, 316:82-91 (2003)), and luminescent proximity assays (see, e.g., U.S. Patent Publication No. 20060063219), as well as any of the techniques described above, can be used to determine the phosphorylation state of at least one tyrosine kinase signaling component in CTCs and CECs.

Example 4

Prediction of Gefitinib-Sensitive Cell Lines Using Artificial Intelligence

This example illustrates that the use of learning statistical classifier systems to combine the information from disparate sample sets results in greater diagnostic power than each set provides alone.

Samples

A nucleic acid and/or protein profile of one or more biomarkers in a set of cancer cell lines was obtained to generate a data file of input values for use in an algorithm to predict whether a particular cell line would be responsive to treatment with gefitinib (Iressa®). As a non-limiting example, the level of EGFR family kinase expression (i.e., HER1-4) and Akt phosphorylation in the breast cancer cell lines described by Moasser et al. (*Cancer Res.*, 61:7184-7188 (2001)) was used to generate a data file of input values for statistical analysis (Table 1). The breast cancer cell lines were BT474, MDA-MB-361, ZR75, T47D, MDA-MIB-231, SkBr3, MDA-MB-453, A431, MDA-MB-468, A549, PC3, SkOv3, DU145, MCF-7, Colo205, T24, and DU4475. One skilled in the art will appreciate that the nucleic acid and/or protein profile of biomarkers of interest can be obtained either prospectively or retrospectively from one or more patient sample sets and used in the algorithms described herein for predicting whether a particular type of tumor would be responsive to gefitinib therapy.

TABLE 1

Data file of input values used in algorithmic analysis of breast cancer cell lines.

| Cell Line | HER1 | HER2 | HER3 | HER4 | $IC_{50}$ | CATAG | Akt | SUB1 | SUB2 |
|---|---|---|---|---|---|---|---|---|---|
| BT474 | 1 | 5000 | 150 | 10 | 0.8 | 1 | 10 | Train | Train |
| MDA-MB-361 | 1 | 1000 | 100 | 2 | 8 | 1 | 20 | Train | Test |
| ZR75 | 0 | 100 | 1 | 3 | 16 | 0 | 85 | Train | Train |
| T47D | 1 | 50 | 200 | 1000 | 12 | 0 | 85 | Train | Test |
| MDA-MIB-231 | 100 | 30 | 0 | 1 | 15 | 0 | 70 | Train | Train |
| SkBr3 | 50 | 5000 | 50 | 3 | 1 | 1 | 2 | Train | Test |
| MDA-MB-453 | 0.5 | 1000 | 200 | 5 | 7 | 1 | 40 | Train | Test |
| A431 | 2000 | 120 | 100 | 0 | 1 | 1 | 2 | Test | Test |
| MDA-MB-468 | 2000 | 0 | 100 | 0 | 13.5 | 0 | 90 | Train | Train |
| A549 | 75 | 90 | 2 | 0 | 12 | 0 | 85 | Test | Train |
| PC3 | 75 | 30 | 0 | 0 | 14 | 0 | 55 | Test | Train |
| SkOv3 | 200 | 2000 | 1 | 20 | 2.5 | 1 | 40 | Test | Train |
| DU145 | 80 | 40 | 1 | 0 | 7 | 1 | 35 | Test | Test |
| MCF-7 | 1 | 40 | 200 | 200 | 15 | 0 | 70 | Train | Train |
| Colo205 | 1 | 200 | 5 | 5 | 12 | 0 | 105 | Test | Test |
| T24 | 50 | 90 | 0 | 0 | 18 | 0 | 90 | Test | Train |
| DU4475 | 0.5 | 0 | 1 | 1 | 10 | 0 | 105 | Test | Test |

The densities of the HER1, HER2, HER3, and HER4 bands in the Western blot from FIG. 1 of Moasser et al. were estimated by naked eye observation and given a relative value ranging from 0 to 5000. The level of Akt activity for each cell line was determined using the data from FIG. 3 of Moasser et al. at a gefitinib concentration of 10 μM. An $IC_{50}$ <9 μM was considered gefitinib-sensitive ("CATAG" = 1).

Statistical Analyses

In this study, two different learning statistical classifiers were used (e.g., random forests and artificial neural networks) to predict sensitivity of the cell lines to gefitinib. These learning statistical classifiers use multivariate statistical methods like, for example, multilayer perceptrons with feed-forward backpropagation that can adapt to complex data and make decisions based strictly on the data presented, without the constraints of regular statistical classifiers.

Random Forests

Each breast cancer cell line sample was randomly selected for random forest (RF) prediction. Out-of-the-bag data was used for testing. Multiple RF models using commercially available software (Salford Systems; San Diego, Calif.) were created and analyzed for accuracy of prediction using the test cohort. The best predictive RF models were selected and tested for accuracy of prediction using data from the validation cohort. The success of the RF prediction is shown in Table 2. Table 3 shows a ranking of the importance of the variables.

TABLE 2

Random forest prediction success.

| Actual Cell Line | Total Cases | Percent Correct | Sensitive N = 7 | Insensitive N = 10 |
|---|---|---|---|---|
| Sensitive | 7 | 100 | 7 | 0 |
| Insensitive | 10 | 100 | 0 | 10 |

TABLE 3

Random forest variable importance.

| Variable | Score | |
|---|---|---|
| Akt | 100.00 | ||||||||||||||||||||||||||||||||||||||||||| |
| HER2 | 30.03 | |||||||||| |
| HER3 | 3.58 | | |
| HER1 | 0.00 | |
| HER4 | 0.00 | |

Artificial Neural Networks

Each breast cancer cell line sample was randomly selected for neural network prediction, with a total of 9 for training and 8 for validation. Different samples were used for training, testing, and for validation purposes. The Intelligent Problem Solver module of the neural networks software package (Statistica; StatSoft, Inc.; Tulsa, Okla.) was used to create artificial neural network (ANN) models in a feed-forward, back-propagation, and classification mode with the training cohort. Linear, multi-layer perceptron (MLP), and probabilistic neural networks (PNN) models are shown in Table 4. The best models were selected based on the lowest error of prediction on the test dataset.

TABLE 4

Neural network prediction accuracy.

| Model | Subset | Sensitive* | Insensitive* |
|---|---|---|---|
| Linear | 1 | 3/3 | 5/5 |
| MLP | 1 | 3/3 | 5/5 |
| PNN | 2 | 4/5 | 3/3 |
| Linear | 3 | 4/4 | 4/4 |
| MLP | 4 | 2/2 | 6/6 |

*= Predicted numbers/observed numbers.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An assay method for predicting the response of a subject diagnosed with a gastrointestinal stromal tumor (GIST) or renal cell carcinoma (RCC) to treatment with sunitinib (Sutent®), said method comprising:

(a) analyzing a sample obtained from said subject to determine the presence or absence of an activating mutation in the c-KIT, PDGFRA, and VEGFR-1 genes and the level of c-KIT, PDGFRA, and VEGFR-1 protein expression in said sample, wherein said activating mutation in the c-KIT gene comprises a deletion, insertion, or single nucleotide substitution in exon 9, 11, 13, or 17 of the c-KIT gene, wherein said activating mutation in the PDGFRA gene comprises a deletion, insertion, or single nucleotide substitution in exon 12, 14, or 18 of the PDGFRA gene, and wherein said activating mutation in the VEGFR-1 gene comprises a deletion, insertion, or single nucleotide substitution in the juxtamembrane domain or the tyrosine kinase domain of the VEGFR-1 gene; and (b) predicting an increased likelihood that said subject will respond to treatment with sunitinib when said activating mutation in at least one of the c-KIT, PDGFRA, and VEGFR-1 genes is present, when at least one of the PDGFRA and VEGFR-1 proteins is overexpressed, and when the c-KIT protein is overexpressed.

2. The method of claim 1, wherein said sample is selected from the group consisting of whole blood, serum, plasma, urine, nipple aspirate, lymph, saliva, fine needle aspirate, tumor tissue, and combinations thereof.

3. The method of claim 2, wherein said sample comprises circulating tumor cells, circulating endothelial cells, circulating endothelial progenitor cells, cancer stem cells, or combinations thereof.

4. The method of claim 1, wherein said method further comprises sending the results from said prediction to a clinician.

5. The method of claim 1, further comprising recommending the administration of sunitinib to said subject when said subject is predicted to have an increased likelihood of responding to treatment with sunitinib.

6. The method of claim 1, further comprising analyzing said sample to determine the presence or absence of an activating mutation in the K-Ras gene when said activating mutation in the c-KIT, PDGFRA, and VEGFR-1 genes is absent and when the c-KIT, PDGFRA, and VEGFR-1 proteins are not overexpressed, wherein said activating mutation in the K-Ras gene results in a substitution in the K-Ras amino acid sequence selected from the group consisting of a cysteine for glycine at position 12 (G12C), a cysteine for glycine at position 13 (G13C), an aspartic acid for glycine at position 12 (G12D), a serine for glycine at position 12 (G12S), and a valine for glycine at position 12 (G12V).

7. The method of claim 6, wherein said subject is predicted to have a decreased likelihood of responding to treatment with sunitinib when said activating mutation in the K-Ras gene is present.

8. The method of claim 7, further comprising recommending the administration of another tyrosine kinase inhibitor or an alternative cancer therapy to said subject.

9. The method of claim 6, further comprising analyzing said sample to determine the presence or absence of Erk (MAPK) and Akt activation and the level of PTEN protein expression when said activating mutation in the K-Ras gene is absent.

10. The method of claim 9, wherein the presence or absence of Erk (MAPK) and Akt activation and the level of PTEN protein expression are each assigned an index value.

11. The method of claim 10, wherein a cumulative index value (CIV) is calculated by summing said index values assigned to the presence or absence of Erk (MAPK) and Akt activation and the level of PTEN protein expression.

12. The method of claim 11, further comprising comparing said CIV to an index cutoff value.

13. The method of claim 12, wherein said subject is predicted to have an increased likelihood of responding to treatment with sunitinib when said CIV is greater than or equal to said index cut-off value.

14. The method of claim 13, further comprising recommending the administration of sunitinib to said subject.

15. The method of claim 12, wherein said subject is predicted to have a decreased likelihood of responding to treatment with sunitinib when said CIV is less than said index cut-off value.

16. The method of claim 15, further comprising recommending the administration of another tyrosine kinase inhibitor or an alternative cancer therapy to said subject.

17. The method of claim 1, wherein the level of c-KIT, PDGFRA, and VEGFR-1 protein expression is determined by immunohistochemistry or an immunoassay.

18. The method of claim 17, wherein said immunoassay comprises an enzyme-linked immunosorbent assay (ELISA).

19. The method of claim 1, wherein the presence or absence of said activating mutation in the c-KIT, PDGFRA, and VEGFR-1 genes is determined by the polymerase chain reaction (PCR).

* * * * *